United States Patent
Yabuguchi

(10) Patent No.: US 12,161,537 B2
(45) Date of Patent: Dec. 10, 2024

(54) WATER-ABSORBENT RESIN PARTICLES, WATER-ABSORBENT ARTICLE, AND METHOD FOR MANUFACTURING SAME

(71) Applicant: SUMITOMO SEIKA CHEMICALS CO., LTD., Hyogo (JP)

(72) Inventor: Hiroki Yabuguchi, Himeji (JP)

(73) Assignee: SUMITOMO SEIKA CHEMICALS CO., LTD., Hyogo (JP)

( * ) Notice: Subject to any disclaimer, the term of this patent is extended or adjusted under 35 U.S.C. 154(b) by 729 days.

(21) Appl. No.: 17/311,608

(22) PCT Filed: Dec. 12, 2019

(86) PCT No.: PCT/JP2019/048818
§ 371 (c)(1),
(2) Date: Jun. 7, 2021

(87) PCT Pub. No.: WO2020/122215
PCT Pub. Date: Jun. 18, 2020

(65) Prior Publication Data
US 2022/0015959 A1 Jan. 20, 2022

(30) Foreign Application Priority Data

Dec. 12, 2018 (JP) .................................. 2018-232851
Jan. 30, 2019 (JP) .................................. 2019-014545
(Continued)

(51) Int. Cl.
*A61F 13/49* (2006.01)
*A61F 13/53* (2006.01)
*A61L 15/24* (2006.01)

(52) U.S. Cl.
CPC .............. *A61F 13/49* (2013.01); *A61F 13/53* (2013.01); *A61L 15/24* (2013.01);
(Continued)

(58) Field of Classification Search
CPC .......... A61F 2013/530788; A61F 13/49; A61F 13/53; A61F 2013/530569;
(Continued)

(56) References Cited

U.S. PATENT DOCUMENTS 5,599,335 A * 2/1997 Goldman ................ A61L 15/42
604/378
6,150,582 A * 11/2000 Wada .................... A61F 13/531
604/385.01
(Continued)

FOREIGN PATENT DOCUMENTS

CN         1856331        11/2006
CN         103272571       9/2013
(Continued)

OTHER PUBLICATIONS

Certificate of Experimental Results Plaintiffs Evidence No. 15, submitted for Japanese Patent Application No. J019-055270, Dec. 17, 2020, 6 pages; English translation provided. (Year: 2020).*
(Continued)

*Primary Examiner* — Andrew J Mensh
(74) *Attorney, Agent, or Firm* — HSML P.C.

(57) ABSTRACT

Water-absorbing resin particles, in which a permeation and spreading index represented by Formula (1) is 10.0 or higher, and a water absorption capacity for a physiological saline solution is 50.0 g/g or more, are disclosed.

Formula (1):

Permeation and spreading index=value of non-pressurization $DW$ after 1 minute (mL/g)+artificial urine permeation speed when water-absorbing resin particles are swollen 10 times (g/min)     (1).

16 Claims, 5 Drawing Sheets

(30) Foreign Application Priority Data

Mar. 22, 2019 (JP) ................................. 2019-055270
Mar. 22, 2019 (JP) ................................. 2019-055332

(52) U.S. Cl.
CPC ............. *A61F 2013/530569* (2013.01); *A61F 2013/530591* (2013.01); *A61F 2013/530737* (2013.01)

(58) Field of Classification Search
CPC .......... A61F 2013/530591; A61F 2013/53073; A61L 15/24
USPC ......................................................... 604/372
See application file for complete search history.

(56) References Cited

U.S. PATENT DOCUMENTS

| | | | | |
|---|---|---|---|---|
| 6,562,879 | B1 * | 5/2003 | Hatsuda | C08J 3/122 528/502 F |
| 2012/0258851 | A1 * | 10/2012 | Nakatsuru | C08J 3/12 502/7 |
| 2014/0031473 | A1 * | 1/2014 | Nogi | C08F 20/06 525/383 |
| 2017/0107313 | A1 * | 4/2017 | Murakami | C08F 2/20 |

FOREIGN PATENT DOCUMENTS

| | | |
|---|---|---|
| EP | 0761241 | 3/1997 |
| EP | 2048184 | 4/2009 |
| EP | 2623198 | 8/2013 |
| EP | 3437732 | 2/2019 |
| EP | 3896096 | 10/2021 |
| EP | 3896122 | 10/2021 |
| JP | H6-345819 | 12/1994 |
| JP | H8-053550 | 2/1996 |
| JP | H9-124955 | 5/1997 |
| JP | H9-510889 | 11/1997 |
| JP | 2003-088552 | 3/2003 |
| JP | 2004-261797 | 9/2004 |
| JP | 2005-111474 | 4/2005 |
| JP | 2006-068731 | 3/2006 |
| JP | 2009-019065 | 1/2009 |
| JP | 2009-531158 | 9/2009 |
| JP | 2012-012451 | 1/2012 |
| JP | 2014-506804 | 3/2014 |
| JP | 5485805 | 5/2014 |
| JP | 2020-093244 | 6/2020 |
| JP | 2020-121089 | 8/2020 |
| WO | 95/026209 | 10/1995 |
| WO | 2004/110328 | 12/2004 |
| WO | 2005/027986 | 3/2005 |
| WO | 2006/014031 | 2/2006 |
| WO | 2006/123561 | 11/2006 |
| WO | 2007/116777 | 10/2007 |
| WO | 2008/015980 | 2/2008 |
| WO | WO-2008015980 A1 * | 2/2008 ............. C08J 3/245 |
| WO | 2012/043821 | 4/2012 |
| WO | 2012/120864 | 9/2012 |
| WO | 2015/129917 | 9/2015 |
| WO | 2016/104374 | 6/2016 |
| WO | WO-2016104374 A1 * | 6/2016 ............... C08F 2/32 |
| WO | 2017/170605 | 10/2017 |
| WO | 2018/155591 | 8/2018 |
| WO | 2018/181565 | 10/2018 |

OTHER PUBLICATIONS

International Search Report of PCT/JP2019/048818, Mar. 10, 2020, 2 pages.
International Preliminary Report on Patentability of PCT/JP2019/048818, Jun. 24, 2021, 8 pages.
The extended European Search Report issued for European Patent Application No. 19896121.1, Sep. 7, 2022, 19 pages.
Argument (Response to Office Action) submitted for Japanese Patent Application No. 2019-055270, Nov. 27, 2019, 8 pages; Partial translation provided.
Argument (Response to Office Action) submitted for Japanese Patent Application No. 2019-055281, Nov. 28, 2019, 20 pages; Partial translation provided.
Fredric L. Buchholz, et al., "Modern Superabsorbent Ploymer Technology", 1998, pp. 69-74, 97-103, 210-213, and 251-257.
"Certificate of Experimental Results Plaintiff's Evidence No. 11", submitted for Japanese Patent Application No. 2019-055270, Dec. 17, 2020, 6 pages; English translation provided.
"Certificate of Experimental Results Plaintiff's Evidence No. 12", submitted for Japanese Patent Application No. 2019-055270, Dec. 17, 2020, 6 pages; English translation provided.
"Certificate of Experimental Results Plaintiff's Evidence No. 13", submitted for Japanese Patent Application No. 2019-055270, Dec. 17, 2020, 8 pages; English translation provided.
"Certificate of Experimental Results Plaintiff's Evidence No. 14", submitted for Japanese Patent Application No. 2019-055270, Dec. 17, 2020, 6 pages; English translation provided.
"Certificate of Experimental Results Plaintiff's Evidence No. 15", submitted for Japanese Patent Application No. 2019-055270, Dec. 17, 2020, 6 pages; English translation provided.
Notice of Reasons of Cancellation issued for Japanese Patent Application No. 2019-055270 (Patent No. 6710302), Apr. 1, 2021, 183 pages; English translation provided.
Argument (Response to Office Action) submitted for Japanese Patent Application No. 2019-055332, Nov. 27, 2019, 23 pages; Partial translation provided.
Notice of Reasons of Cancellation issued for Japanese Patent Application No. 2019-055332 (Patent No. 6710303), Mar. 31, 2021, 17 pages; English translation provided.

* cited by examiner

WATER-ABSORBENT RESIN PARTICLES, WATER-ABSORBENT ARTICLE, AND METHOD FOR MANUFACTURING SAME

TECHNICAL FIELD

The present invention relates to water-absorbing resin particles, an absorbent article, and a method for manufacturing the absorbent article.

BACKGROUND ART

Conventionally, an absorbent containing water-absorbing resin particles has been used in an absorbent article for absorbing a liquid containing water such as urine as a main component. For example, Patent Literature 1 below discloses a method for producing water-absorbing resin particles having a particle size that enables them to be suitably used for an absorbent article such as a diaper, and Patent Literature 2 below discloses a method of using a hydrogel-absorbent polymer having Saline Flow Conductivity, performance under pressure, and the like as an effective absorbent member for accommodating various body fluids such as urine.

CITATION LIST

Patent Literature

[Patent Literature 1] Japanese Unexamined Patent Publication No. H6-345819
[Patent Literature 2] Published Japanese Translation No. H09-510889 of the PCT International Publication

SUMMARY OF INVENTION

Technical Problem

An absorbent article formed from a conventional absorbent has room for improvement in leakage properties in which because an absorption target liquid is not sufficiently absorbed by the absorbent, a phenomenon (liquid running) in which the excess liquid flows on a surface of the absorbent is likely to occur, and as a result, the liquid is leaked to the outside of the absorbent article.

An object of one aspect of the present invention is to provide water-absorbing resin particles capable of inhibiting liquid leakage from an absorbent. An object of another aspect of the present invention is to provide an absorbent article in which liquid leakage is inhibited, and a method for manufacturing the same.

Solution to Problem

The inventors of the present invention have thought that it is important to make it easier for a liquid, which comes into contact with an assemblage of water-absorbing resin particles contained in an absorbent, to permeate into and spread on the entire assemblage to ameliorate liquid leakage from the absorbent and an absorbent article. As a result of diligent research, they have found that liquid leakage from the absorbent and the absorbent article is affected by a water absorption speed (DW) of the water-absorbing resin particles and a liquid permeation speed during a short period of time (initial stage) after the liquid comes into contact with the assemblage of the water-absorbing resin particles, and therefore have completed the present invention.

One aspect of the present invention provides water-absorbing resin particles in which a permeation and spreading index represented by Formula (1) is 10.0 or higher, and a water absorption capacity for a physiological saline solution is 50.0 g/g or more.

Formula (1):

$$\text{Permeation and spreading index} = \text{value of non-pressurization } DW \text{ after 1 minute (mL/g)} + \text{artificial urine permeation speed when water-absorbing resin particles are swollen 10 times g/min} \quad (1)$$

The non-pressurization DW is a water absorption speed represented by an amount of a physiological saline solution (a saline solution having a concentration of 0.9% by mass) absorbed by the water-absorbing resin particles under no pressurization until the elapse of a predetermined time after the water-absorbing resin particles are brought into contact with the physiological saline solution. The non-pressurization DW is represented by an amount of absorption (mL) per 1 g of the water-absorbing resin particles before absorbing a physiological saline solution. The value of non-pressurization DW after 1 minute means an amount of absorption 1 minute after the water-absorbing resin particles are brought into contact with a physiological saline solution. The value of non-pressurization DW after 1 minute is an index showing a water absorption speed during a short period of time (initial stage) after the water-absorbing resin particles come into contact with a liquid. The artificial urine permeation speed when the water-absorbing resin particles are swollen 10 times is an index showing liquid permeability of the water-absorbing resin particles that have absorbed a certain amount of a liquid in the initial stage. Therefore, a value of the permeation and spreading index, which is the sum of those two values, reflects a water absorption speed in the initial stage and liquid permeability after water absorption. According to the findings of the inventors of the present invention, when a permeation and spreading index is high, it means that a liquid, which has come into contact with an assemblage of the water-absorbing resin particles, easily permeates into and spreads on the entire assemblage. It is thought that by making it easier for a liquid to permeate into and spread on the entire assemblage of the water-absorbing resin particles, the water-absorbing resin particles can inhibit liquid leakage. That is, the water-absorbing resin particles can effectively contribute to inhibiting occurrence of liquid leakage from an absorbent article.

The permeation and spreading index may be 13.0 or higher. In this case, liquid leakage is further inhibited.

Another aspect of the present invention provides an absorbent article including a liquid-impermeable sheet, an absorbent, and a liquid-permeable sheet. The liquid-impermeable sheet, the absorbent, and the liquid-permeable sheet are disposed in this order. The absorbent contains the above-described water-absorbing resin particles. A permeation and spreading index of the water-absorbing resin particles represented by Formula (1) is 10.0 or higher.

Formula (1):

$$\text{Permeation and spreading index} = \text{value of non-pressurization } DW \text{ after 1 minute (mL/g)} + \text{artificial urine permeation speed when water-absorbing resin particles are swollen 10 times (g/min)} \quad (1)$$

A water absorption capacity of the water-absorbing resin particles for a physiological saline solution is 50.0 g/g or more.

The permeation and spreading index may be 13.0 or higher. In this case, liquid leakage is further inhibited.

Still another aspect of the present invention provides a method for manufacturing an absorbent article. The method according to the present invention include: sorting out water-absorbing resin particles in which a permeation and spreading index is 10.0 or higher, and a water absorption capacity for a physiological saline solution is 50.0 g or more; and disposing an absorbent containing the sorted water-absorbing resin particles between a liquid-impermeable sheet and a liquid-permeable sheet. According to this method, it is possible to manufacture an absorbent article in which occurrence of liquid leakage is inhibited.

Advantageous Effects of Invention

According to the one aspect of the present invention, it is possible to provide water-absorbing resin particles capable of inhibiting liquid leakage. According to the other aspect of the present invention, it is possible to provide an absorbent article in which liquid leakage is inhibited.

DESCRIPTION OF EMBODIMENTS

Figure 1:
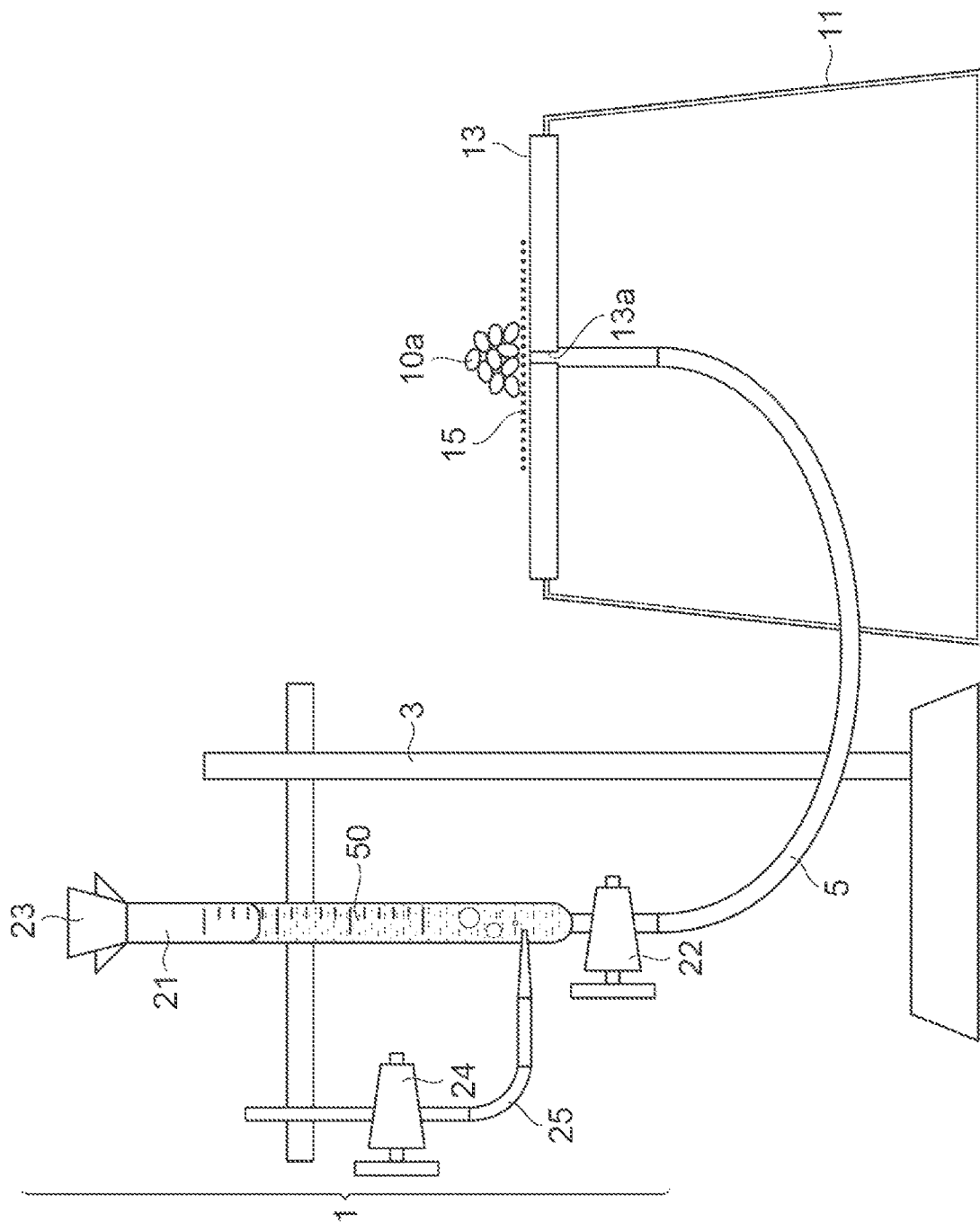
FIG. 1 is a schematic view showing a measuring device for a value of non-pressurization DW after 1 minute.

Hereinafter, embodiments of the present invention will be described in detail. However, the present invention is not limited to the following embodiments, and can be variously modified and implemented within the scope of the gist thereof.

In the present specification, "acrylic" and "methacrylic" are collectively referred to as "(meth)acrylic." "Acrylate" and "methacylate" are also referred to as "(meth)acrylate." Regarding numerical value ranges described in a stepwise manner in the present specification, an upper limit value or a lower limit value of a numerical value range in a certain step can be arbitrarily combined with an upper limit value or a lower limit value of a numerical value range in another step. In a numerical value range described in the present specification, an upper limit value or a lower limit value of the numerical value range may be replaced with a value shown in examples. It is sufficient for the expression "A or B" to include any one of A and B, and it may include both of them. The term "water-soluble" means that a solubility of 5% by mass or more is exhibited in water at 25° C. For materials exemplified in the present specification, one kind may be used alone, or two or more kinds may be used in combination. In a case where there are a plurality of substances corresponding to each of components in a composition, a content of each of the components in the composition means a total amount of the plurality of substances present in the composition unless otherwise specified.

Water-absorbing resin particles according to the present embodiment show a permeation and spreading index of 10.0 or higher. A permeation and spreading index is represented by Formula (1).

Permeation and spreading index=value of non-pressurization $DW$ after 1 minute (mL/g)+artificial urine permeation speed when water-absorbing resin particles are swollen 10 times (g/min)    (1)

A permeation and spreading index is 10.0 or higher, and from the viewpoint of further inhibiting liquid leakage, it may be 11.0 or higher, 12.0 or higher, 13.0 or higher, 14.0 or higher, 15.0 or higher, 16.0 or higher, 17.0 or higher, 18.0 or higher, 19.0 or higher, 20.0 or higher, 21.0 or higher, or 21.5 or higher, and it may be 30.0 or lower, 25.0 or lower, or 22.0 or lower. From the viewpoint of further inhibiting liquid leakage, a permeation and spreading index may be, for example, 10.0 or higher and 30.0 or lower, 11.0 or higher and 30.0 or lower, 12.0 or higher and 25.0 or lower, 13.0 or higher and 25.0 or lower, 14.0 or higher and 25.0 or lower, 15.0 or higher and 22.0 or lower, 16.0 or higher and 22.0 or lower, or 17.0 or higher and 22.0 or lower.

From the viewpoint of further inhibiting liquid leakage, a value of non-pressurization DW after 1 minute in Formula (1) may be 3.0 mL/g or more, 5.0 mL/g or more, 7.0 mL/g or more, 9.0 mL/g or more, 11.0 mL/g or more 13.0 mL/g or more, 15.0 mL/g or more, 17.0 mL/g or more, or 18.0 mL/g or more, and it may be 30 mL/g or less, 25 mL/g or less, or 20 mL/g or less. The value (mL/g) of non-pressurization DW after 1 minute is a value measured by a method described in Examples to be described later.

From the viewpoint of further inhibiting liquid leakage, an artificial urine permeation speed in Formula (1) when the water-absorbing resin particles are swollen 10 times may be 0.5 g/min or more, 1.0 g/min or more, 1.5 g/min or more, 2.0 g/min or more, or 3.0 g/min or more, and it may be 20.0 g/min or less, 15.0 g/min or less, or 12.5 g/min or less. The artificial urine permeation speed when the water-absorbing resin particles are swollen 10 times is defined as a value measured by a method described in Examples to be described later. In the present specification, the artificial urine is an aqueous solution consisting of 0.780% by mass of sodium chloride, 0.022% by mass of calcium chloride, 0.038% by mass of magnesium sulfate, 0.002% by mass of Blue No. 1, and water.

A water absorption capacity for a physiological saline solution is 50.0 g/g or more, and from the viewpoint of further inhibiting liquid leakage, it may be 51.0 g/g or more, 52.0 g/g or more, 53.0 g/g or more, 54.0 g/g or more, or 55.0 g/g or more, and it may be 70 g/g or less, 67 g/g or less, 65 g/g or less, 62 g/g or less, or 60 g/g or less. The water absorption capacity for a physiological saline solution is measured by a method described in Examples to be described later.

A water absorption capacity of the water-absorbing resin particles according to the present embodiment for a physiological saline solution under a load may be, for example, 10 to 40 mL/g, 15 to 35 mL/g, 20 to 30 mL/g, or 22 to 28 mL/g. As the water absorption capacity for a physiological saline solution under a load, water absorption capacity (25° C.) at a load of 4.14 kPa can be used. The water absorption capacity can be measured by a method described in Examples to be described later.

Examples of shapes of the water-absorbing resin particles according to the present embodiment include a substantially spherical shape, a crushed shape, and a granular shape. A median particle size of the water-absorbing resin particles according to the present embodiment may be 250 to 850 μm, 300 to 700 μm, or 300 to 600 μm. The water-absorbing resin particles according to the present embodiment may have a desired particle size distribution at a timing obtained in a production method to be described later, but their particle size distribution may be adjusted by performing operations such as adjustment of a particle size through classification with a sieve.

The water-absorbing resin particles according to the present embodiment can contain, for example, a crosslinked polymer formed by polymerization of monomers including ethylenically unsaturated monomers. The crosslinked polymer has a monomer unit derived from an ethylenically unsaturated monomer.

The water-absorbing resin particles can be produced by a method including a step of polymerizing monomers including ethylenically unsaturated monomers. Examples of methods of polymerization include a reverse-phase suspension polymerization method, an aqueous solution polymerization method, a bulk polymerization method, and a precipitation polymerization method. Among them, the polymerization method may be the reverse-phase suspension polymerization method or the aqueous solution polymerization method from the viewpoints of facilitating securement of favorable water absorption characteristics of the obtained water-absorbing resin particles and control of a polymerization reaction. Hereinbelow, a method for polymerizing ethylenically unsaturated monomers will be described with the reverse-phase suspension polymerization method as an example.

An ethylenically unsaturated monomer may be water-soluble. Examples thereof include (meth)acrylic acid and a salt thereof, 2-(meth)acrylamide-2-methylpropanesulfonic acid and a salt thereof, (meth)acrylamide, N,N-dimethyl (meth)acrylamide, 2-hydroxyethyl (meth)acrylate, N-methylol (meth)acrylamide, polyethylene glycol mono(meth)acrylate, N,N-diethylaminoethyl (meth)acrylate, N,N-diethylaminopropyl (meth)acrylate, and diethylaminopropyl (meth)acrylamide. In a case where an ethylenically unsaturated monomer has an amino group, the amino group may be quaternized. The ethylenically unsaturated monomer may be used alone or in a combination of two or more kinds thereof. A functional group, such as a carboxyl group and an amino group, of the monomer, may function as a crosslinkable functional group in a surface crosslinking process to be described later.

Among them, from the viewpoint of high industrial availability, the ethylenically unsaturated monomer may include at least one compound selected from the group consisting of (meth)acrylic acid and a salt thereof, acrylamide, methacrylamide, and N,N-dimethyl acrylamide, or may include at least one compound selected from the group consisting of (meth)acrylic acid and a salt thereof and acrylamide. The ethylenically unsaturated monomer may include at least one compound selected from the group consisting of (meth) acrylic acid and a salt thereof from the viewpoint of further enhancing water absorption characteristics.

The ethylenically unsaturated monomer may be used in a form of an aqueous solution. A concentration of the ethylenically unsaturated monomers in an aqueous solution containing the ethylenically unsaturated monomers (hereinafter, simply referred to as an "aqueous solution of monomers") may be 20% by mass or more and a saturated concentration or less, may be 25% to 70% by mass, or may be 30% to 55% by mass. Examples of water to be used an aqueous solution include tap water, distilled water, and ion exchange water.

For the monomer for obtaining the water-absorbing resin particles, a monomer other than the above-described ethylenically unsaturated monomers may be used. Such a monomer can be used by, for example, being mixed with an aqueous solution containing the above-described ethylenically unsaturated monomers. A usage amount of the ethylenically unsaturated monomers may be 70 to 100 mol %, may be 80 to 100 mol %, may be 90 to 100 mol %, may be 95 to 100 mol %, or may be 100 mol %, with respect to a total amount of monomers. Among them, a proportion of (meth)acrylic acid and a salt thereof may be 70 to 100 mol %, may be 80 to 100 mol %, may be 90 to 100 mol %, may be 95 to 100 mol %, or may be 100 mol %, with respect to a total amount of monomers.

In a case where ethylenically unsaturated monomers have an acidic group, an aqueous solution of monomers may be used after neutralizing this acidic group with an alkaline neutralizing agent. From the viewpoint of increasing an osmotic pressure of the obtained water-absorbing resin particles and thereby further enhancing water absorption characteristics (such as a water absorption capacity), a degree of neutralization in the ethylenically unsaturated monomers by the alkaline neutralizing agent may be 10 to 100 mol %, may be 50 to 90 mol %, or may be 60 to 80 mol % of the acidic group in the ethylenically unsaturated monomers. Examples of alkaline neutralizing agents include alkali metal salts such as sodium hydroxide, sodium carbonate, sodium hydrogen carbonate, potassium hydroxide, and potassium carbonate; and ammonia. The alkaline neutralizing agent may be used alone or in combination of two or more kinds thereof. The alkaline neutralizing agent may be used in a form of an aqueous solution to simplify a neutralizing operation. Neutralization of the acidic groups in the ethylenically unsaturated monomers can be performed by, for example, adding an aqueous solution of sodium hydroxide, potassium hydroxide, or the like dropwise to the above-described aqueous solution of monomers and mixing them.

In the reverse-phase suspension polymerization method, an aqueous solution of monomers can be dispersed in a hydrocarbon dispersion medium in the presence of a surfactant, and polymerization of ethylenically unsaturated monomers can be performed using a radical polymerization initiator or the like. As the radical polymerization initiator, it is possible to use a water-soluble radical polymerization initiator.

Examples of surfactants include nonionic surfactants and anionic surfactants. Examples of nonionic surfactants include sorbitan fatty acid esters, (poly)glycerin fatty acid esters (where "(poly)" means both of a case with the prefix "poly" and a case without the prefix "poly," and the same applies hereinbelow), sucrose fatty acid esters, polyoxyethylene sorbitan fatty acid esters, polyoxyethylene glycerin fatty acid esters, sorbitol fatty acid esters, polyoxyethylene sorbitol fatty acid esters, polyoxyethylene alkyl ethers, polyoxyethylene alkylphenyl ethers, polyoxyethylene castor oil, polyoxyethylene hydrogenated castor oil, alkylallyl formaldehyde condensed polyoxyethylene ethers, polyoxyethylene polyoxypropylene block copolymers, polyoxyethylene polyoxypropyl alkyl ethers, and polyethylene glycol fatty acid esters. Examples of anionic surfactants include fatty acid salts, alkylbenzene sulfonate, taurate, polyoxyethylene alkylphenyl ether sulfuric acid ester salts, polyoxyethylene alkyl ether sulfonic acid salts, phosphoric acid esters of polyoxyethylene alkyl ethers, and phosphoric acid esters of polyoxyethylene alkyl allyl ethers. The surfactant may be used alone or in combination of two or more kinds thereof.

The surfactant may include at least one compound selected from the group consisting of sorbitan fatty acid esters, polyglycerin fatty acid esters, and sucrose fatty acid esters, from the viewpoints that then, a state of a W/O type reverse-phase suspension becomes favorable, water-absorbing resin particles having a suitable particle size are easily obtained, and industrial availability becomes high. The surfactant may include sucrose fatty acid esters or may include sucrose stearic acid esters from the viewpoint that water absorption characteristics of the obtained water-absorbing resin particles are then easily improved.

A usage amount of the surfactant may be 0.05 to 10 parts by mass, may be 0.08 to 5 parts by mass, or may be 0.1 to 3 parts by mass, with respect to 100 parts by mass of the aqueous solution of monomers, from the viewpoint that a sufficient effect is obtained within these usage amounts, and these amounts are economic.

In the reverse-phase suspension polymerization, a polymeric dispersant may be used in combination with the above-mentioned surfactant. Examples of polymeric dispersants include maleic anhydride-modified polyethylene, maleic anhydride-modified polypropylene, a maleic anhydride-modified ethylene-propylene copolymer, a maleic anhydride-modified EPDM (ethylene propylene diene terpolymer), maleic anhydride-modified polybutadiene, a maleic anhydride-ethylene copolymer, a maleic anhydride-propylene copolymer, a maleic anhydride-ethylene-propylene copolymer, a maleic anhydride-butadiene copolymer, polyethylene, polypropylene, an ethylene-propylene copolymer, oxidized polyethylene, oxidized polypropylene, an oxidized ethylene-propylene copolymer, an ethylene-acrylic acid copolymer, ethyl cellulose, ethyl hydroxyethyl cellulose, and the like. The polymeric dispersant may be used alone or in combination of two or more kinds thereof. From the viewpoint of better dispersion stability of monomers, the polymeric dispersant may be at least one selected from the group consisting of maleic anhydride-modified polyethylene, maleic anhydride-modified polypropylene, a maleic anhydride-modified ethylene-propylene copolymer, a maleic anhydride-ethylene copolymer, a maleic anhydride-propylene copolymer, a maleic anhydride-ethylene-propylene copolymer, polyethylene, polypropylene, an ethylene-propylene copolymer, oxidized polyethylene, oxidized polypropylene, and an oxidized ethylene-propylene copolymer.

A usage amount of the polymeric dispersant may be 0.05 to 10 parts by mass, may be 0.08 to 5 parts by mass, or may be 0.1 to 3 parts by mass, with respect to 100 parts by mass of the aqueous solution of monomers, from the viewpoint that a sufficient effect is obtained within these usage amounts, and these amounts are economic.

The hydrocarbon dispersion medium may include at least one compound selected from the group consisting of a chained aliphatic hydrocarbon having 6 to 8 carbon atoms and an alicyclic hydrocarbon having 6 to 8 carbon atoms. Examples of hydrocarbon dispersion media include chained aliphatic hydrocarbons such as n-hexane, n-heptane, 2-methylhexane, 3-methylhexane, 2,3-dimethylpentane, 3-ethylpentane, and n-octane; alicyclic hydrocarbons such as cyclohexane, methylcyclohexane, cyclopentane, methylcyclopentane, trans-1,2-dimethylcyclopentane, cis-1,3-dimethylcyclopentane, and trans-1,3-dimethylcyclopentane; and aromatic hydrocarbons such as benzene, toluene, and xylene. The hydrocarbon dispersion medium may be used alone or in combination of two or more kinds thereof.

For the hydrocarbon dispersion medium, at least one selected from the group consisting of n-heptane and cyclohexane may be contained from the viewpoints of high industrial availability and stable qualities. Furthermore, from the same viewpoints, as a mixture of the hydrocarbon dispersion media, for example, a commercially available Exxsol Heptane (manufactured by ExxonMobil Chemical: containing n-heptane and 75% to 85% of hydrocarbons of isomers thereof) may be used.

A usage amount of the hydrocarbon dispersion medium may be 30 to 1,000 parts by mass, may be 40 to 500 parts by mass, or may be 50 to 300 parts by mass, with respect to 100 parts by mass of the aqueous solution of monomers, from the viewpoint that polymerization heat is then appropriately removed, and thereby a polymerization temperature is easily controlled. In a case where a usage amount of the hydrocarbon dispersion medium is 30 parts by mass or more, there is a tendency that it becomes easy to control a polymerization temperature. In a case where a usage amount of the hydrocarbon dispersion medium is 1,000 parts by mass or less, there is a tendency that productivity of polymerization is improved, which is economic.

A radical polymerization initiator may be water-soluble. Examples thereof include persulfates such as potassium persulfate, ammonium persulfate, and sodium persulfate; peroxides such as methyl ethyl ketone peroxide, methyl isobutyl ketone peroxide, di-t-butyl peroxide, t-butyl cumyl peroxide, t-butyl peroxyacetate, t-butyl peroxyisobutyrate, t-butyl peroxypivalate, and hydrogen peroxide; and azo compounds such as 2,2'-azobis(2-amidinopropane) dihydrochloride, 2,2'-azobis[2-(N-phenylamidino)propane] dihydrochloride, 2,2'-azobis[2-(N-allylamidino)propane] dihydrochloride, 2,2'-azobis[2-(2-imidazolin-2-yl)propane] dihydrochloride, 2,2'-azobis{2-[1-(2-hydroxyethyl)-2-imidazolin-2-yl]propane}dihydrochloride, 2,2'-azobis{2-methyl-N-[1,1-bis(hydroxymethyl)-2-hydroxyethyl]propionamide}, 2,2'-azobis[2-methyl-N-(2-hydroxyethyl)-propionamide], and 4,4'-azobis(4-cyanoyaleric acid). The radical polymerization initiator may be used alone or in combination of two or more kinds thereof. The radical polymerization initiator may be at least one selected from the group consisting of potassium persulfate, ammonium persulfate, sodium persulfate, 2,2'-azobis(2-amidinopropane) dihydrochloride, 2,2'-azobis[2-(2-imidazolin-2-yl) propane] dihydrochloride, and 2,2'-azobis {2-[1-(2-hydroxyethyl)-2-imidazolin-2-yl]propane}dihydrochloride.

A usage amount of the radical polymerization initiator may be 0.00005 to 0.01 moles with respect to 1 mole of the ethylenically unsaturated monomers. A case in which a usage amount of the radical polymerization initiator is 0.00005 moles or more is efficient, because then a polymerization reaction is not required to be performed for a long period of time. In a case where a usage amount of the radical polymerization initiator is 0.01 moles or less, it is easy to inhibit occurrence of a rapid polymerization reaction.

The radical polymerization initiator can also be used as a redox polymerization initiator when it is used in combination with a reducing agent such as sodium sulfite, sodium hydrogen sulfite, ferrous sulfate, and L-ascorbic acid.

In a polymerization reaction, an aqueous solution of monomers used for the polymerization may contain a chain transfer agent. Examples of chain transfer agents include hypophosphites, thiols, thiolic acids, secondary alcohols, and amines.

The aqueous solution of monomers used for the polymerization may contain a thickener to control a particle size of the water-absorbing resin particles. Examples of thickeners include hydroxyethyl cellulose, hydroxypropyl cellulose, methyl cellulose, carboxymethyl cellulose, polyacrylic acid, polyethylene glycol, polyacrylamide, polyethyleneimine, dextrin, sodium alginate, polyvinyl alcohol, polyvinylpyrrolidone, polyethylene oxide, and the like. In a case where stirring speeds in the polymerization are the same, a median particle size of particles to be obtained is likely to become large as a viscosity of the aqueous solution of monomers becomes high.

Crosslinking may occur by self-crosslinking upon the polymerization, but crosslinking may be carried out by further using an internal crosslinking agent. By using the internal crosslinking agent, it is easy to control water absorption characteristics of the water-absorbing resin particles. The internal crosslinking agent is generally added to a reaction solution in the polymerization reaction. Examples of internal crosslinking agents include di- or tri(meth)acrylic acid esters of polyols such as ethylene glycol, propylene glycol, trimethylolpropane, glycerin, polyoxyethylene glycol, polyoxypropylene glycol, and polyglycerin; unsaturated polyesters obtained by reacting the polyols with unsaturated acids (such as maleic acid and fumaric acid); bis(meth)acrylamides such as N,N'-methylenebis(meth)acrylamide; di- or tri(meth)acrylic acid esters obtained by reacting a polyepoxide with (meth)acrylic acid; carbamyl di(meth)acrylate esters obtained by reacting a polyisocyanate (such as tolylene diisocyanate and hexamethylene diisocyanate) with hydroxyethyl (meth)acrylate; compounds having two or more polymerizable unsaturated groups, such as allylated starch, allylated cellulose, diallyl phthalate, N, N', N''-triallyl isocyanurate, and divinylbenzene; polyglycidyl compounds such as (poly)ethylene glycol diglycidyl ether, (poly)propylene glycol diglycidyl ether, (poly)glycerin diglycidyl ether, (poly)glycerin triglycidyl ether, (poly)propylene glycol polyglycidyl ether, and polyglycerol polyglycidyl ether; haloepoxy compounds such as epichlorohydrin, epibromohydrin, and α-methyl epichlorohydrin; compounds having two or more reactive functional groups, such as isocyanate compounds (such as 2,4-tolylene diisocyanate and hexamethylene diisocyanate); and the like. The internal crosslinking agent may be used alone or in combination of two or more kinds thereof. The internal crosslinking agent may be a polyglycidyl compound, may be a diglycidyl ether compound, or may be at least one selected from the group consisting of (poly)ethylene glycol diglycidyl ether, (poly)propylene glycol diglycidyl ether, and (poly)glycerin diglycidyl ether.

A usage amount of the internal crosslinking agent may be 0 mmol or more, 0.02 mmol or more, 0.03 mmol or more, 0.04 mmol or more, or 0.05 mmol or more, and may be 0.1 moles or less, per 1 mole of the ethylenically unsaturated monomer, from the viewpoints of inhibiting water-soluble properties by appropriately crosslinking the obtained polymer, and easily obtaining a sufficient water absorption capacity. In particular, in first-stage polymerization in multi-stage reverse phase suspension polymerization, when an amount of the internal crosslinking agent is 0.03 mmol or more per 1 mole of the ethylenically unsaturated monomer, it is easy to obtain water-absorbing resin particles having a high permeation and spreading index.

An aqueous phase containing an ethylenically unsaturated monomer, a radical polymerization initiator, and if necessary, an internal crosslinking agent, and the like; and an oil phase containing a hydrocarbon dispersant, and if necessary, a surfactant and a polymeric dispersant, and the like can be heated under stirring in a state where they are mixed to carry out reverse-phase suspension polymerization in a water-in-oil system.

When performing the reverse-phase suspension polymerization, an aqueous solution of monomers which contains ethylenically unsaturated monomers is dispersed in a hydrocarbon dispersion medium in the presence of a surfactant (and if necessary, a polymeric dispersant). In this case, a timing of adding the surfactant, the polymeric dispersant, or the like before the start of the polymerization reaction may be either before or after the addition of the aqueous solution of monomers.

Among them, the polymerization may be carried out after dispersing the aqueous solution of monomers in the hydrocarbon dispersion medium in which the polymeric dispersant has been dispersed, and then further dispersing the surfactant in the hydrocarbon dispersion medium, from the viewpoint that an amount of the hydrocarbon dispersion medium remaining in the obtained water-absorbing resin can then be easily reduced.

The reverse-phase suspension polymerization can be carried out in one stage or in multiple stages of two or more stages. The reverse-phase suspension polymerization may be carried out in two or three stages from the viewpoint of increasing productivity.

In a case where reverse-phase suspension polymerization is carried out in multiple stages of two or more stages, it is sufficient for stages after a second stage of reverse-phase suspension polymerization to be carried out in the same manner as in a first stage of reverse-phase suspension polymerization by adding ethylenically unsaturated monomers to a reaction mixture obtained in the first stage of polymerization reaction and mixing them, after performing the first stage of reverse-phase suspension polymerization. In reverse-phase suspension polymerization in each stage after the second stage, reverse-phase suspension polymerization may be carried out by adding, in addition to ethylenically unsaturated monomers, the above-mentioned radical polymerization initiator within a range of molar ratios of the respective components to the ethylenically unsaturated monomers, based on an amount of ethylenically unsaturated monomers added during reverse-phase suspension polymerization in each stage after the second stage. If necessary, the internal crosslinking agent may be used in reverse-phase suspension polymerization in each stage after the second stage. In a case where the internal crosslinking agent is used, reverse-phase suspension polymerization may be carried out by adding the internal crosslinking agent within a range of molar ratios of the respective components to the ethylenically unsaturated monomers based on an amount of ethylenically unsaturated monomers provided in each stage.

A temperature for the polymerization reaction varies depending on radical polymerization initiators used, but it may be 20° C. to 150° C., or may be 40° C. to 120° C., from the viewpoint that the polymerization is then promptly performed, which shortens a polymerization time, and thereby economic efficiency increases, and that polymerization heat is then easily removed, and thereby the reaction is smoothly performed. A reaction time is generally 0.5 to 4 hours. Completion of the polymerization reaction can be confirmed from, for example, stop of temperature rising in the reaction system. Accordingly, a polymer of ethylenically unsaturated monomers is generally obtained in a state of a hydrous gel polymer.

After the polymerization, post-polymerization crosslinking may be carried out by adding a crosslinking agent to the obtained hydrous gel polymer and heating them. By performing the post-polymerization crosslinking, a degree of crosslinking of the hydrous gel polymer can be increased, and thereby water absorption characteristics of the water-absorbing resin particles can be further improved.

Examples of crosslinking agents for performing the post-polymerization crosslinking include polyols such as ethylene glycol, propylene glycol, 1,4-butanediol, trimethylolpropane, glycerin, polyoxyethylene glycol, polyoxypropylene glycol, and polyglycerin; compounds having two or more epoxy groups, such as (poly)ethylene glycol diglycidyl ether, (poly)propylene glycol diglycidyl ether, and (poly)glycerin diglycidyl ether; haloepoxy compounds such as epichlorohydrin, epibromohydrin, and α-methyl epichlorohydrin; compounds having two or more isocyanate groups such as 2,4-tolylene diisocyanate and hexamethylene diisocyanate; oxazoline compounds such as 1,2-ethylenebisoxazoline; carbonate compounds such as ethylene carbonate; and hydroxyalkylamide compounds such as bis[N,N-di(β-hydroxyethyl)]adipamide. Among them, the crosslinking agent may be polyglycidyl compounds such as (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether. These crosslinking agents may be used alone or in combination of two or more kinds thereof.

An amount of the crosslinking agent used in the post-polymerization crosslinking may be 0 to 0.03 moles, may be 0 to 0.01 moles, or may be 0.00001 to 0.005 moles in a molar ratio, per 1 mole of the water-soluble ethylenically unsaturated monomer, from the viewpoint of exhibiting suitable water absorption characteristics by appropriately crosslinking the obtained hydrous gel polymer. In a case where an amount of the crosslinking agent used in the post-polymerization crosslinking is within the above range, it is possible to easily obtain water-absorbing resin particles having a high permeation and spreading index.

It is sufficient for a timing for adding the post-polymerization crosslinking to be after polymerization of ethylenically unsaturated monomers used for the polymerization. In a case of multi-stage polymerization, the crosslinking agent may be added after the multi-stage polymerization. From the viewpoint of a water content (to be described later), the crosslinking agent for the post-polymerization crosslinking may be added within a region of [water content immediately after polymerization±3% by mass], in consideration of heat generation during and after polymerization, retention due to process delay, system opening when a crosslinking agent is added, and fluctuation in moisture content due to addition of water associated with addition of a crosslinking agent.

Subsequently, drying is performed to remove moisture from the obtained hydrous gel polymer. By drying, polymer particles containing the polymer of ethylenically unsaturated monomers are obtained. Examples of drying methods include a method (a) in which a hydrous gel polymer in a state of being dispersed in a hydrocarbon dispersion medium is subjected to azeotropic distillation by heating from the outside, and the hydrocarbon dispersion medium is refluxed to remove moisture; a method (b) in which a hydrous gel polymer is taken out by decantation and dried under reduced pressure; and a method (c) in which a hydrous gel polymer is separated by filtration with a filter and dried under reduced pressure. Among them, the method (a) may be generally used for its simplicity in a production process.

It is possible to adjust a particle size of the water-absorbing resin particles by adjusting a rotational speed of a stirrer during the polymerization reaction or by adding a flocculating agent to the system after the polymerization reaction or at an initial time of drying. A particle size of the obtained water-absorbing resin particle can be increased by adding the flocculating agent. As the flocculating agent, an inorganic flocculating agent can be used. Examples of inorganic flocculating agents (for example, powdery inorganic flocculating agents) include silica, zeolite, bentonite, aluminum oxide, talc, titanium dioxide, kaolin, clay, and hydrotalcite. The flocculating agent may be at least one selected from the group consisting of silica, aluminum oxide, talc, and kaolin from the viewpoint of a flocculation effect.

In the reverse-phase suspension polymerization, a method of adding the flocculating agent may be a method in which a flocculating agent is dispersed in a hydrocarbon dispersion medium of the same kind as that used in the polymerization, or water in advance, and then the mixture is mixed into a hydrocarbon dispersion medium containing a hydrous gel polymer under stirring.

An amount of the flocculating agent added may be 0.001 to 1 part by mass, may be 0.005 to 0.5 parts by mass, or may be 0.01 to 0.2 parts by mass, with respect to 100 parts by mass of ethylenically unsaturated monomers used in the polymerization. By setting an amount of the flocculating agent added to be within the above range, it is easy to obtain water-absorbing resin particles having a desired particle size distribution.

In the production of the water-absorbing resin particles, a surface portion of the hydrous gel polymer may be crosslinked surface-crosslinked) using a crosslinking agent in the drying process or any of subsequent processes. By performing surface crosslinking, it is easy to control water absorption characteristics of the water-absorbing resin particles. The surface crosslinking may be performed at a timing when the hydrous gel polymer has a specific water content. A timing of the surface crosslinking may be a time point at which a water content of the hydrous gel polymer is 5% to 50% by mass, may be a time point at which a water content thereof is 10% to 40% by mass, or may be a time point at which a water content thereof is 15% to 35% by mass. A water content (% by mass) of the hydrous gel polymer is calculated by the following formula.

$$\text{Water content}=[Ww/(Ww+Ws)]\times 100$$

Ww: An amount of water of a hydrous gel polymer obtained by adding an amount of water used, as desired, upon mixing a flocculating agent, a surface crosslinking agent, and the like to an amount obtained by subtracting an amount of water extracted to the outside of the system by the drying process from an amount of water contained in an aqueous solution of monomers before polymerization in the all polymerization processes.

Ws: A solid fraction calculated from an amount of materials introduced, such as ethylenically unsaturated monomers, a crosslinking agent, and an initiator, each of which constitutes the hydrous gel polymer.

Examples of crosslinking agents (surface crosslinking agents) for performing surface crosslinking include compounds having two or more reactive functional groups. Examples of crosslinking agents include polyols such as ethylene glycol, propylene glycol, 1,4-butanediol, trimethylolpropane, glycerin, polyoxyethylene glycol, polyoxypropylene glycol, and polyglycerin; polyglycidyl compounds such as (poly)ethylene glycol diglycidyl ether, (poly)glycerin diglycidyl ether, (poly)glycerin triglycidyl ether, trimethylolpropane triglycidyl ether, (poly)propylene glycol polyglycidyl ether, and (poly)glycerol polyglycidyl ether; haloepoxy compounds such as epichlorohydrin, epibromohydrin, and α-methyl epichlorohydrin; isocyanate compounds such as 2,4-tolylene diisocyanate and hexamethylene diisocyanate; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds such as 1,2-ethylenebisoxazoline; carbonate compounds such as ethylene carbonate; hydroxyalkylamide compounds such as bis[N,N-di(β-hydroxyethyl)]adipamide; and the like. The crosslinking agent may be used alone or in combination of two or more kinds thereof. The crosslinking agent may be a polyglycidyl compound, or may be at least one selected from the group consisting of (poly)ethylene glycol diglycidyl ether, (poly)glycerin diglycidyl ether, (poly)glycerin triglycidyl ether, (poly)propylene glycol polyglycidyl ether, and polyglycerol polyglycidyl ether.

In general, a usage amount of the surface crosslinking agent may be 0.00001 to 0.02 moles, may be 0.00005 to 0.01 moles, or may be 0.0001 to 0.005 moles, with respect to 1 mole of the ethylenically unsaturated monomer used in the polymerization, from the viewpoint of exhibiting suitable water absorption characteristics by appropriately crosslinking the obtained hydrous gel polymer. In a case where a usage amount of the surface crosslinking agent is 0.00001 moles or more, a crosslinking density in a surface portion of the water-absorbing resin particles is sufficiently increased, and thereby gel strength of the water-absorbing resin particles is easily increased. In a case where a usage amount of the surface crosslinking agent is 0.02 moles or less, a water absorption capacity of the water-absorbing resin particles is easily increased. Furthermore, in a case where a usage amount of the surface crosslinking agent is within the above range, it is possible to easily obtain water-absorbing resin particles having a high permeation and spreading index.

It is possible to obtain polymer particles, which are a dried product of surface-crosslinked water-absorbing resin particles, by distilling off water and the hydrocarbon dispersion medium by a known method after the surface crosslinking.

The water-absorbing resin particles according to the present embodiment may be composed of only the polymer particles, but they can further contain, for example, various additional components selected from gel stabilizers, metal chelating agents (ethylenediaminetetraacetic acid and its salts, diethylenetriaminepentaacetic acid and its salts, for example, diethylenetriaminepentaacetic acid pentasodium, and the like), and flowablility improvers (lubricants). The additional components may be disposed inside the polymer particles, on a surface of the polymer particles, or both of the inside and on the surface thereof. The additional component may be flowablility improvers (lubricants), and among them, it may be inorganic particles. Examples of inorganic particles include silica particles such as amorphous silica.

The water-absorbing resin particles may contain a plurality of inorganic particles disposed on the surface of the polymer. The inorganic particles can be disposed on the surface of the polymer particles by, for example, mixing the polymer particles and the inorganic particles. These inorganic particles may be silica particles such as amorphous silica. In a case where the water-absorbing resin particles contain inorganic particles disposed on the surface of the polymer particles, a ratio of the inorganic particles to a mass of the polymer particles may be 0.2% by mass or more, 0.5% by mass or more, 1.0% by mass or more, or 1.5% by mass or more, and it may be 5.0% by mass or less or 3.5% by mass or less. The inorganic particles referred to herein generally have a minute size as compared with a size of the polymer particles. For example, an average particle size of the inorganic particles may be 0.1 to 50 μm, 0.5 to 30 μm, or 1 to 20 μm. The average particle size referred to herein can be a value measured by a dynamic light scattering method or a laser diffraction/scattering method. By setting an amount of the inorganic particles added to be within the above range, it is easy to obtain water-absorbing resin particles having a suitable permeation and spreading index among water absorption characteristics of the water-absorbing resin particles.

An absorbent according to one embodiment contains the water-absorbing resin particles according to the present embodiment. The absorbent according to the present embodiment can contain a fibrous material, and it is, for example, a mixture containing the water-absorbing resin particles and the fibrous material. The configuration of the absorbent may be, for example, a configuration in which water-absorbing resin particles and the fibrous materials are uniformly mixed, a configuration in which water-absorbing resin particles are held between fibrous materials formed in a sheet shape or a layer shape, or another configuration.

Examples of fibrous materials include finely pulverized wood pulp; cotton; cotton linter; rayon; cellulose-based fibers such as cellulose acetate; synthetic fibers such as polyamides, polyesters, and polyolefins; a mixture of these fibers; and the like. The fibrous material may be used alone or in combination of two or more kinds thereof. As the fibrous material, hydrophilic fibers can be used.

A mass proportion of the water-absorbing resin particles in the absorbent with respect to a total amount of the water-absorbing resin particles and the fibrous material may be 2% to 100% by mass, 10% to 80% by mass, or 20% to 60% by mass.

Fibers may be adhered to each other by adding an adhesive binder to the fibrous material in order to enhance shape retention properties before or during use of the absorbent. Examples of adhesive binders include thermal bonding synthetic fibers, hot-melt adhesives, and adhesive emulsions. The adhesive hinder may be used alone or in combination of two or more kinds thereof.

Examples of thermal bonding synthetic fibers include full-melt binders such as polyethylene, polypropylene, and an ethylene-propylene copolymer; partial-melt binders formed of polypropylene and polyethylene in a side-by-side or core-and-sheath configuration; and the like. In the above-mentioned partial-melt binders, only a polyethylene portion can be thermal-bonded.

Examples of hot-melt adhesives include a mixture of a base polymer such as an ethylene-vinyl acetate copolymer, a styrene-isoprene-styrene block copolymer, a styrene-butadiene-styrene block copolymer, a styrene-ethylene-butylene-styrene block copolymer; a styrene-ethylene-propylene-styrene block copolymer; and an amorphous polypropylene with a viscosity imparting agent, a plasticizer, an antioxidant, or the like.

Examples of adhesive emulsions include polymers of at least one monomer selected from the group consisting of methyl methacrylate, styrene, acrylonitrile, 2-ethylhexyl acrylate, butyl acrylate, butadiene, ethylene, and vinyl acetate.

The absorbent according to the present embodiment may contain inorganic powders (for example, amorphous silica), deodorants, pigments, dyes, antibacterial agents, fragrances, pressure sensitive adhesives, and the like, all of which are generally used in the technical field. These additives can impart various functions to the absorbent. Examples of inorganic particles include silicon dioxide, zeolite, kaolin, clay, and the like. In a case where the water-absorbing resin particles contain inorganic particles, the absorbent may contain an inorganic powder in addition to the inorganic particles in the water-absorbing resin particles.

A shape of the absorbent according to the present embodiment is not particularly limited, but it may be, for example, a sheet shape. A thickness of the absorbent (for example, a thickness of a sheet-shaped absorbent) may be, for example, 0.1 to 20 mm or 0.3 to 15 mm.

An absorbent article according to the present embodiment includes the absorbent according to the present embodiment. Examples of the absorbent article according to the present embodiment include a core wrap that retains the shape of the absorbent; a liquid-permeable sheet disposed on the outermost part on a side from which an absorption target liquid is infiltrated; a liquid-impermeable sheet disposed on the outermost part on a side opposite to the side from which the absorption target liquid is infiltrated; and the like. Examples of the absorbent article include diapers (for example, paper diapers), toilet training pants, incontinence pads, hygiene products (sanitary napkins, tampons, and the like), sweat pads, pet sheets, portable toilet members, animal excrement treatment materials, and the like.

Figure 3:
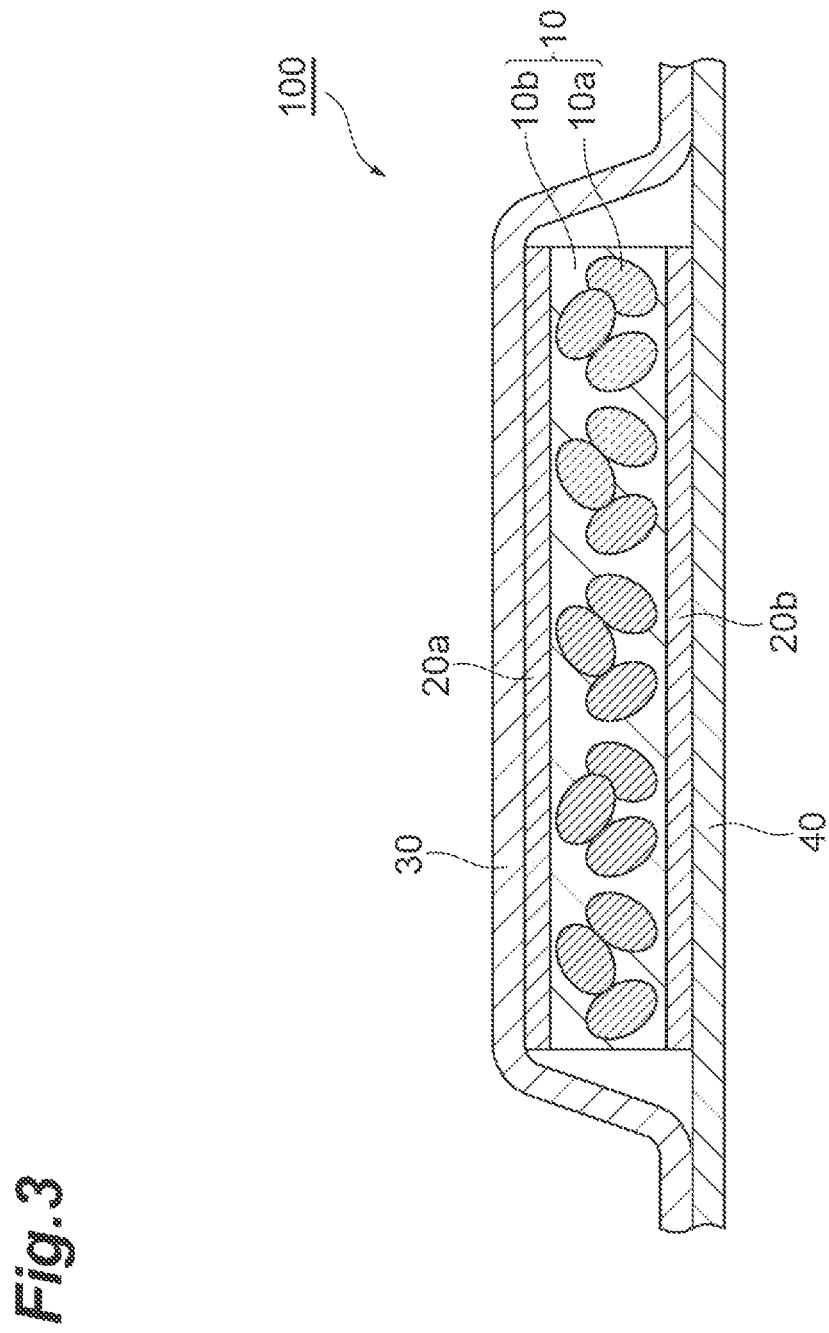
FIG. 3 is a cross-sectional view showing an example of an absorbent article.

FIG. 3 is a cross-sectional view showing an example of an absorbent article. An absorbent article 100 shown in FIG. 3 includes an absorbent 10, core wraps 20a and 20b, a liquid-permeable sheet 30, and a liquid-impermeable sheet 40. In the absorbent article 100, the liquid-impermeable sheet 40, the core wrap 20b, the absorbent 10, the core wrap 20a, and the liquid-permeable sheet 30 are laminated in this order. In FIG. 3, there is a portion shown to be a gap between the members, but the members may be in close contact with each other without the gap.

The absorbent 10 has water-absorbing resin particles 10a according to the present embodiment and a fiber layer 10b containing a fibrous material. The water-absorbing resin particles 10a are dispersed in the fiber layer 10b.

A content of the water-absorbing resin particles 10a may be 100 to 1,000 g per square meter of the absorbent 10 (that is, 100 to 1,000 g/m$^2$), may be 150 to 800 g/m$^2$, or may be 200 to 700 g/m$^2$, from the viewpoint that sufficient liquid absorption performances can then be more easily obtained when the absorbent 10 is used for the absorbent article 100. A content of the water-absorbing resin particles 10a may be 100 g/m$^2$ or more from the viewpoint of exhibiting sufficient liquid absorption performances as the absorbent article 100 and thereby inhibiting, particularly liquid leakage. A content of the water-absorbing resin particles 10a may be 1,000 g/m$^2$ or less from the viewpoint of inhibiting occurrence of a gel blocking phenomenon, and thereby exhibiting a diffusion performance of a liquid as the absorbent article 100 and further improving a permeation speed of the liquid.

A content of the fibrous material may be 50 to 800 g per square meter of the absorbent 10 (that is, 50 to 800 g/m$^2$), may be 100 to 600 g/m$^2$, or may be 150 to 500 g/m$^2$, from the viewpoint that sufficient) liquid absorption performances are then obtained when the absorbent 10 is used for the absorbent article 100. A content of the fibrous material may be 50 g or more per square meter of the absorbent 10 (that is, 50 g/m$^2$ or more) from the viewpoint of exhibiting sufficient liquid absorption performances as the absorbent article 100, and thereby particularly inhibiting occurrence of a gel blocking phenomenon to improve a diffusion performance of a liquid, and increasing strength of the absorbent 10 after it absorbs a liquid. A content of the fibrous material may be 800 g or less per square meter of the absorbent 10 (that is, 800 g/m$^2$ or less) from the viewpoint of particularly inhibiting reversion after liquid absorption.

The core wrap 20a is disposed on one surface side of the absorbent 10 (an upper side of the absorbent 10 in FIG. 3) in a state of being in contact with the absorbent 10. The core wrap 20b is disposed on the other surface side of the absorbent 10 (a lower side of the absorbent 10 in FIG. 3) in a state of being in contact with the absorbent 10. The absorbent 10 is disposed between the core wrap 20a and the core wrap 20b. Examples of the core wraps 20a and 20b include tissues, non-woven fabrics, and the like. The core wrap 20a and the core wrap 20b each have, for example, a main surface having the same size as that of the absorbent 10.

The liquid-permeable sheet 30 is disposed on the outermost part on a side from which an absorption target liquid is infiltrated. The liquid-permeable sheet 30 is disposed on the core wrap 20a in a state of being in contact with the core wrap 20a. The liquid-impermeable sheet 40 is disposed on the outermost part on a side opposite to the liquid-permeable sheet 30, in the absorbent article 100. The liquid-impermeable sheet 40 is disposed below the core wrap 20b in a state of being in contact with the core wrap 20b. The liquid-permeable sheet 30 and the liquid-impermeable sheet 40 each have, for example, a main surface wider than the main surface of the absorbent 10, and outer edges of the liquid-permeable sheet 30 and the liquid-impermeable sheet 40 respectively extend around the absorbent 10 and the core wraps 20a and 20b.

A magnitude relationship between the absorbent 10, the core wraps 20a and 20b, the liquid-permeable sheet 30, and the liquid-impermeable sheet 40 is not particularly limited, and it is appropriately adjusted according to usage applications and the like of the absorbent article. A shape of the absorbent 10 shown in FIG. 3 is maintained by being sandwiched between the two core wraps 20a and 20b. A method of maintaining a shape of the absorbent by the core wrap is not limited thereto, and for example, the absorbent may be sandwiched between one core wrap that has been folded. The core wrap may form a bag, and the absorbent may be disposed inside the bag.

The liquid-permeable sheet 30 may be a sheet formed of resin or fiber generally used in the technical field. From the viewpoint of liquid permeability, flexibility, and strength when the liquid-permeable sheet 30 is used in an absorbent article, the liquid-permeable sheet 30 may contain, for example, synthetic resins such as polyolefins such as polyethylene (PE) and polypropylene (PP); polyesters such as polyethylene terephthalate (PET), polytrimethylene terephthalate (PTT), and polyethylene naphthalate (PEN); polyamides such as nylon; and rayon, or synthetic fibers containing these synthetic resins, or the liquid-permeable sheet 30 may be natural fibers including cotton, silk, hemp, or pulp (cellulose). The liquid-permeable sheet 30 may contain synthetic fibers from the viewpoint of increasing strength of the liquid-permeable sheet 30. Synthetic fibers may be particularly polyolefin fibers, polyester fibers, or a combination thereof. These materials may be used alone or in combination of two or more materials.

The liquid-permeable sheet 30 may be a non-woven fabric, a porous sheet, or a combination thereof. Non-woven fabric is a sheet in which fibers are entwined instead of being woven. The non-woven fabric may be a non-woven fabric (short-fiber non-woven fabric) composed of short fibers (that is, staples), or may be a non-woven fabric (long-fiber non-woven fabric) composed of long fibers (that is, filaments). In general, staples may have a fiber length of several hundred millimeters or shorter, but its length is not limited thereto.

The liquid-permeable sheet 30 may be thermal bonded non-woven fabrics, air through non-woven fabrics, resin bonded non-woven fabrics, spunbond non-woven fabrics, melt-blown non-woven fabrics, airlaid non-woven fabrics, spunlace non-woven fabrics, point-bonded non-woven fabrics, or a laminate of two or more of non-woven fabrics selected from these non-woven fabrics. These non-woven fabrics can be, for example, non-woven fabrics formed of the above-mentioned synthetic fibers or natural fibers. The laminate of two or more of non-woven fabrics may be, for example, a spunbond/melt-blown/spunbond non-woven fabric that is a composite non-woven fabric having spunbond non-woven fabric, melt-blown non-woven fabric, and spunbond non-woven fabric, which are laminated in this order. The liquid-permeable sheet 30 may be a thermal bonded non-woven fabric, an air through non-woven fabric, a spunbond non-woven fabric, or a spunbond/melt-blown/spunbond non-woven fabric, from the viewpoint of inhibiting liquid leakage.

It is desirable that a non-woven fabric used as the liquid-permeable sheet 30 have appropriate hydrophilicity from the viewpoint of liquid absorption performances of the absorbent article. From this viewpoint, the liquid-permeable sheet 30 may be a non-woven fabric having a hydrophilicity of 5 to 200 as measured according to a measurement method of Pulp and Paper Test Method No. 68 (2000) by the Japan Technical Association of Pulp and Paper Industry. The hydrophilicity of the non-woven fabric may be 10 to 150. For details of Pulp and Paper Test Method No. 68, for example, WO2011/086843 can be referred to.

The hydrophilic non-woven fabric as described above may be formed of fibers, such as rayon fibers, showing appropriate hydrophilicity, or may be formed of fibers obtained by hydrophilizing hydrophobic chemical fibers such as polyolefin fibers and polyester fibers. Examples of methods of obtaining a non-woven fabric containing hydrophobic chemical fibers that have been hydrophilized include a method of obtaining a non-woven fabric by a spunbond technique using a mixture in which a hydrophilizing agent is added to hydrophobic chemical fibers, a method of using a hydrophilizing agent when producing a spunbond non-woven fabric from hydrophobic chemical fibers, and a method of impregnating a spunbond non-woven fabric obtained by using hydrophobic chemical fibers with a hydrophilizing agent. As the hydrophilizing agent, the following examples are used: anionic surfactants such as aliphatic sulfonic acid salts and higher alcohol sulfuric acid ester salts; cationic surfactants such as quaternary ammonium salts; nonionic surfactants such as polyethylene glycol fatty acid esters, polyglycerin fatty acid esters, and sorbitan fatty acid esters; silicone surfactants such as polyoxyalkylene-modified silicone; stain release agents formed of polyester-based, polyamide-based, acrylic-based, or urethane-based resin; and the like.

The liquid-permeable sheet 30 may be a non-woven fabric that is moderately bulky and has a large fabric weight per unit area from the viewpoint of imparting favorable liquid permeability, flexibility, strength, and cushioning properties to an absorbent article, and from the viewpoint of accelerating a liquid penetration speed of an absorbent article. A fabric weight per unit area of the non-woven fabric used for the liquid-permeable sheet 30 may be 5 to 200 g/m$^2$, may be 8 to 150 g/m$^2$, or may be 10 to 100 g/m$^2$. A thickness of the non-woven fabric used for the liquid-permeable sheet 30 may be 20 to 1,400 μm, may be 50 to 1,200 μm, or may be 80 to 1,000 μm.

The liquid-impermeable sheet 40 is disposed on the outermost part on a side opposite to the liquid-permeable sheet 30, in the absorbent article 100. The liquid-impermeable sheet 40 is disposed below the core wrap 20b in a state of being in contact with the core wrap 20b. The liquid-impermeable sheet 40 has, for example, a main surface wider than the main surface of the absorbent 10, and an outer edge of the liquid-impermeable sheet 40 extends around the absorbent 10 and the core wraps 20a and 20b. The liquid-impermeable sheet 40 prevents a liquid absorbed by the absorbent 10 from leaking to the outside from the liquid-impermeable sheet 40 side.

Examples of the liquid-impermeable sheet 40 include sheets made of synthetic resins such as polyethylene, polypropylene, and polyvinyl chloride; sheets made of non-woven fabric such as a spunbond/melt-blown/spunbond (SMS) non-woven fabric in which a water-resistant melt blown non-woven fabric is sandwiched between high-strength spunbond non-woven fabrics; sheets made of a composite material of these synthetic resins and non-woven fabric (for example, spunbond non-woven fabric and spunlace non-woven fabric); and the like. The liquid-impermeable sheet 40 may have breathability from the viewpoint that dampness generated when wearing the absorbent article is then reduced, and thereby discomfort to a wearer can be reduced. As the liquid-impermeable sheet 40, it is possible to use a sheet made of a synthetic resin mainly composed of a low density polyethylene (LDPE) resin. The liquid-impermeable sheet 40 may be, for example, a sheet made of a synthetic resin and having a fabric weight per unit area of 10 to 50 g/m$^2$ from the viewpoint of ensuring flexibility so as not to impair a sensation of wearing the absorbent article.

The absorbent article 100 can be manufactured by, for example, a method including disposing the absorbent 10 between the core wraps 20a, 20b, and disposing them between the liquid-permeable sheet 30 and the liquid-impermeable sheet 40. A laminate, in which the liquid-impermeable sheet 40, the core wrap 20b, the absorbent 10, the core wrap 20a, and the liquid-permeable sheet 30 are laminated in this order, is pressurized as necessary.

The absorbent 10 is formed by mixing the water-absorbing resin particles 10a with the fibrous material. The absorbent 10 may be formed by sorting out and selectively using water-absorbing resin particles in which a permeation and spreading index is 10.0 or higher, and a water absorption capacity for a physiological saline solution is 50.0 g or more.

According to the present embodiment, it is possible to provide a method of absorbing a liquid using the water-absorbing resin particles, absorbent, or absorbent article according to the present embodiment. The method of absorbing a liquid according to the present embodiment includes a step of bringing an absorption target liquid into contact with the water-absorbing resin particles, absorbent, or absorbent article according to the present embodiment.

EXAMPLES

Hereinafter, the present invention will be described in more detail with reference to examples, but the present invention is not limited to these examples.

<Production of Water-Absorbing Resin Particles>

[Production of Water-Absorbing Resin Particles of Example 1]

First-Stage Polymerization Reaction

A cylindrical round-bottomed separable flask was prepared, which had an inner diameter of 11 cm and an internal capacity of 2 L, and was equipped with a reflux condenser, a dropping funnel, a nitrogen gas introduction tube, and as a stirrer, a stirring blade having four inclined paddle blades, each having a blade diameter of 5 cm, in a two-tier manner. 293 g of n-heptane, and 0.736 g of a maleic anhydride-modified ethylene-propylene copolymer (HI-WAX 1105A, manufactured by Mitsui Chemicals, Inc.) as a polymeric dispersant were put into this flask. The reaction solution in the flask was heated to 80° C. while being stirred to dissolve the polymeric dispersant in the n-heptane. Thereafter, the reaction solution was cooled to 50° C.

92.0 g (1.03 moles) of an aqueous solution of acrylic acid at a concentration of 80.5% by mass was put into a beaker with an internal capacity of 300 mL 147.7 g of an aqueous solution of sodium hydroxide at a concentration of 20.9% by mass was added dropwise into the aqueous solution of acrylic acid while cooling the beaker from the outside, and thereby 75 mol % of acrylic acid was neutralized. Then, 0.092 g of hydroxylethyl cellulose (HEC AW-15F, manufactured by Sumitomo Seika Chemicals Co., Ltd.) as a thickener, 0.0736 g (0.272 mmol) of potassium persulfate as a water-soluble radical polymerization initiator, and 0.010 g (0.057 mmol) of ethylene glycol diglycidyl ether as an internal crosslinking agent were dissolved in the solution of acrylic acid. Thereby, a first-stage aqueous solution of monomers was prepared.

The first-stage aqueous solution of monomers was added into the above-mentioned reaction solution in the separable flask, and the reaction solution was stirred for 10 minutes. Then, a surfactant solution containing 6.62 g of n-heptane and 0.736 g of sucrose stearic acid ester (HLB: 3, manufactured by Mitsubishi-Chemical Foods Corporation, RYOTO Sugar Ester S-370) was added into the reaction solution. While stirring the reaction solution at 550 rpm as a rotational speed of the stirring blade, the inside of the system was sufficiently replaced with nitrogen. Thereafter, a polymerization reaction was caused to proceed for 60 minutes while heating the separable flask in a water bath at 70° C. By this polymerization reaction, a first-stage polymerization slurry liquid containing a hydrous gel polymer was obtained.

Second-Stage Polymerization Reaction 128.8 g (1.43 moles) of an aqueous solution of acrylic acid at a concentration of 80.5% by mass was put into a beaker with an internal capacity of 500 mL. 159.0 g of an aqueous solution of sodium hydroxide at a concentration of 27% by mass was added dropwise into the aqueous solution of acrylic acid while cooling the beaker from the outside, and thereby 75 mol % of acrylic acid was neutralized. Then, 0.090 g (0.334 mmol) of potassium persulfate was dissolved in the aqueous solution of acrylic acid. Thereby, a second-stage aqueous solution of monomers was prepared.

While stirring the first-stage polymerization slurry liquid in the separable flask at 1,000 rpm as a rotational speed of the stirring blade, the separable flask was cooled to 25° C. Then, a total amount of the second-stage aqueous solution of monomers was added thereinto, and then the inside of the system was replaced with nitrogen over 30 minutes. Thereafter, a polymerization reaction was caused to proceed for 60 minutes while heating the separable flask in a water bath at 70'C. 0.580 g (0.067 mmol) of an aqueous solution of 2% by mass ethylene glycol diglycidyl ether was added as a crosslinking agent for post-polymerization crosslinking, and thereby a hydrous gel polymer was obtained.

0.265 g of an aqueous solution of diethylenetriaminepentaacetic acid pentasodium at a concentration of 45% by mass was added into the reaction solution containing the hydrous gel polymer under stirring. Thereafter, the flask was immersed in an oil bath set to 125° C., and 247.9 g of water was extracted out of the system by azeotropic distillation with n-heptane and water. Thereafter, 4.42 g (0.507 mmol) of an aqueous solution of ethylene glycol diglycidyl ether at a concentration of 2% by mass as a surface crosslinking agent was added into the reaction solution, and a crosslinking reaction by a surface crosslinking agent was caused to proceed at 83° C. for 2 hours.

From the reaction solution obtained after the surface crosslinking reaction, n-heptane was distilled off by heating at 125° C. to obtain polymer particles (dried product). The polymer particles were passed through a sieve having an aperture of 850 μm. Thereafter, 0.5% by mass of amorphous silica (Oriental Silicas Corporation, Tokusil NP-S) with respect to a mass of the polymer particles was mixed with the polymer particles, and thereby 231.0 g of water-absorbing resin particles containing the amorphous silica was obtained. A median particle size of the water-absorbing resin particles was 355 μm.

[Production of Water-Absorbing Resin Particles of Example 2]

229.2 g of water-absorbing resin particles containing amorphous silica was obtained in the same procedure as in Example 1 except that an amount of water extracted from a reaction solution containing a hydrous gel polymer by azeotropic distillation was 239.7 g. A median particle size of the water-absorbing resin particles was 377 μm.

[Production of Water-Absorbing Resin Particles of Example 3]

Polymer particles (dried product) were obtained in the same procedure as in Example 1 except that, in the first-stage polymerization reaction, a water-soluble radical polymerization initiator was changed to 0.092 g (0.339 mmol) of 2,2'-azobis(2-amidinoproparte) dihydrochloride and 0.018 g (0.068 mmol) of potassium persulfate; in the second-stage polymerization reaction, a water-soluble radical polymerization initiator was changed to 0.129 g (0.475 mmol) of 2,2'-azobis(2-amidinoproparte) dihydrochloride and 0.026 g (0.095 mmol) of potassium persulfate; and an amount of water extracted from a reaction solution containing a hydrous gel polymer by azeotropic distillation was 238.5 g. 0.2% by mass of amorphous silica (Oriental Silicas Corporation, Tokusil NP-S) with respect to a mass of the polymer particles (dried product) was mixed with the polymer particles, and thereby 232.1 g of water-absorbing resin particles containing the amorphous silica was obtained. A median particle size of the water-absorbing resin particles was 396 μm.

[Production of Water-Absorbing Resin Particles of Example 4]

Polymer particles (dried product) were obtained in the same procedure as in Example 1 except that, in the first-stage polymerization reaction, a water-soluble radical polymerization initiator was changed to 0.092 g (0.339 mmol) of 2,2'-azobis(2-amidinopropane) dihydrochloride and 0.018 g (0.068 mmol) of potassium persulfate; in the second-stage polymerization reaction, a water-soluble radical polymerization initiator was changed to 0.129 g (0.475 mmol) of 2,2'-azobis(2-amidinopropane) dihydrochloride and 0.026 g (0.095 mmol) of potassium persulfate; and an amount of water extracted from a reaction solution containing a hydrous gel polymer by azeotropic distillation was 238.5 g.

2.0% by mass of amorphous silica (Oriental Silicas Corporation, Tbkusil NP-S) with respect to a mass of the polymer particles (dried product) was mixed with the polymer particles, and thereby 232.2 g of water-absorbing resin particles containing the amorphous silica was obtained. A median particle size of the water-absorbing resin particles was 393 μm.

[Production of Water-Absorbing Resin Particles of Comparative Example 1]

Polymer particles (dried product) were obtained in the same procedure as in Example 1 except that, in a second-stage polymerization reaction, 0.090 g (0.334 mmol) of potassium persulfate, and as an internal crosslinking agent, 0.0116 g (0.067 mmol) of ethylene glycol diglycidyl ether were dissolved in an aqueous solution of acrylic acid; a crosslinking agent for post-polymerization crosslinking was not added; and an amount of water extracted from a reaction solution containing a hydrous gel polymer by azeotropic distillation was 256.1 g.

0.1% by mass of amorphous silica (Oriental Silicas Corporation, Tokusil NP-S) with respect to a mass of the polymer particles (dried product) was mixed with the polymer particles, and thereby 230.8 g of water-absorbing resin particles containing the amorphous silica was obtained. A median particle size of the water-absorbing resin particles was 349 μm.

[Production of Water-Absorbing Resin Particles of Comparative Example 2]

Polymer particles (dried product) were obtained in the same procedure as in Example 1 except that, in a first-stage polymerization reaction, a water-soluble radical polymerization initiator was changed to 0.092 g (0.339 mmol) of 2,2'-azobis(2-amidinopropane) dihydrochloride and 0.018 g (0.068 mmol) of potassium persulfate, and an internal crosslinking agent was changed to 0.0046 g (0.026 mmol) of ethylene glycol diglycidyl ether; in the second-stage polymerization reaction, a water-soluble radical polymerization initiator was changed to 0.129 g (0.475 mmol) of 2,2'-azobis(2-amidinopropane) dihydrochloride and 0.026 g (0.095 mmol) of potassium persulfate, and an internal crosslinking agent was changed to 0.0116 g (0.067 mmol) of ethylene glycol diglycidyl ether; a crosslinking agent for post-polymerization crosslinking was not added; and an amount of water extracted from a reaction solution containing a hydrous gel polymer by azeotropic distillation was 234.2 g.

0.2% by mass of amorphous silica (Oriental Silicas Corporation, Tokusil NP-S) with respect to a mass of the polymer particles was mixed with the polymer particles, and thereby 229.6 g of water-absorbing resin particles containing the amorphous silica was obtained. A median particle size of the water-absorbing resin particles was 355 μm.

[Production of Water-Absorbing Resin Particles of Comparative Example 3]

Polymer particles (dried product) were obtained in the same procedure as in Example 1 except that, in a first-stage polymerization reaction, a water-soluble radical polymerization initiator was changed to 0.092 g (0.339 mmol) of 2,2'-azobis(2-amidinopropane) dihydrochloride and 0.018 g (0.068 mmol) of potassium persulfate, and an internal crosslinking agent was changed to 0.0046 g (0.026 mmol) of ethylene glycol diglycidyl ether; in the second-stage polymerization reaction, a water-soluble radical polymerization initiator was changed to 0.129 g (0.475 mmol) of 2,2'-azobis(2-amidinopropane) dihydrochloride and 0.026 g (0.095 mmol) of potassium persulfate, and an internal crosslinking agent was changed to 0.0116 g (0.067 mmol) of ethylene glycol diglycidyl ether; a crosslinking agent for post-polymerization crosslinking was not added; and an amount of water extracted from a reaction solution containing a hydrous gel polymer by azeotropic distillation was 223.7 g.

0.2% by mass of amorphous silica (Oriental Silicas Corporation, Tokusil NP-S) with respect to a mass of the polymer particles was mixed with the polymer particles, and thereby 229.6 g of water-absorbing resin particles containing the amorphous silica was obtained. A median particle size of the water-absorbing resin particles was 346 μm.

[Production of Water-Absorbing Resin Particles of Comparative Example 4]

Polymer particles (dried product) were obtained in the same procedure as in Example 1 except that, in a first-stage polymerization reaction, a water-soluble radical polymerization initiator was changed to 0.092 g (0.339 mmol) of 2,2'-azobis(2-amidinopropane) dihydrochloride and 0.018 g (0.068 mmol) of potassium persulfate, and an internal crosslinking agent was changed to 0.0046 g (0.026 mmol) of ethylene glycol diglycidyl ether; in the second-stage polymerization reaction, a water-soluble radical polymerization initiator was changed to 0.129 g (0.475 mmol) of 2,2'-azobis(2-amidinopropane) dihydrochloride and 0.026 g (0.095 mmol) of potassium persulfate, and an internal crosslinking agent was changed to 0.0116 g (0.067 mmol) of ethylene glycol diglycidyl ether; a crosslinking agent for post-polymerization crosslinking was not added; an amount of water extracted from a reaction solution containing a hydrous gel polymer by azeotropic distillation was 219.2 g; and a post-crosslinking agent was changed to 6.62 g (0.761 mmol) of an aqueous solution of ethylene glycol diglycidyl ether at a concentration of 2% by mass.

0.2% by mass of amorphous silica (Oriental Silicas Corporation, Tokusil NP-S) with respect to a mass of the polymer particles was mixed with the polymer particles, and thereby 229.6 g of water-absorbing resin particles containing the amorphous silica was obtained. A median particle size of the water-absorbing resin particles was 356 μm.

<Median Particle Size>

50 g of the water-absorbing resin particles was used for measuring a median particle size.

JIS standard sieves were combined in the following order from the top: a sieve having an aperture of 850 μm, a sieve having an aperture of 500 nm, a sieve having an aperture of 425 μm, a sieve having an aperture of 300 μm, a sieve having an aperture of 250 μm, a sieve having an aperture of 180 μm, a sieve having an aperture of 150 μm, and a receiving tray.

The water-absorbing resin particles were fed to the topmost sieve among the combination of the sieves, shaken for 20 minutes using a Ro-Tap shaker, and thereby classified. After the classification, a mass of the water-absorbing resin particles remaining on each of the sieves was calculated as a mass percentage with respect to a total amount to determine a particle size distribution. By integrating values on the sieves in descending order of the particle sizes with regard to the particle size distribution, a relationship between the aperture of the sieve and the integrated value of mass percentages of the water-absorbing resin particles remaining on the sieve was plotted on a log-probability paper. The plotted points on the probability paper were connected with straight lines, and a particle size corresponding to 50% by mass of the integrated mass percentage was taken as a median particle size.

<Water Absorption Capacity for Physiological Saline Solution (g/g)>

500 g of an aqueous solution of 0.9% by mass sodium chloride (physiological saline solution) was weighed into a beaker having a capacity of 500 mL, and while stirring the solution with a magnetic stirrer bar (8 intriφx30 mm, without a ring) at 600 r/min, 2.0 g of water-absorbing resin particles was dispersed therein such that a lump was not generated. The mixture was left to stand for 60 minutes in a stirred state to cause the water-absorbing resin particles to swell sufficiently. Thereafter, a mass Wa (g) of a standard sieve having an aperture of 75 μm was measured in advance, and using this sieve, the content of the beaker was filtered. The sieve was left to stand for 30 minutes in an inclined state with an inclination angle of about 30 degrees with respect to the horizontal to separate and filter excess water. A mass Wb (g) of the sieve containing the swollen gel was measured, and a water absorption capacity for the physiological saline solution was obtained by the following formula.

Water absorption capacity for physiological saline solution=$(Wb-Wa)/2.0$

<Water Absorption Capacity of Water-Absorbing Resin Particles under Load>

Figure 4:
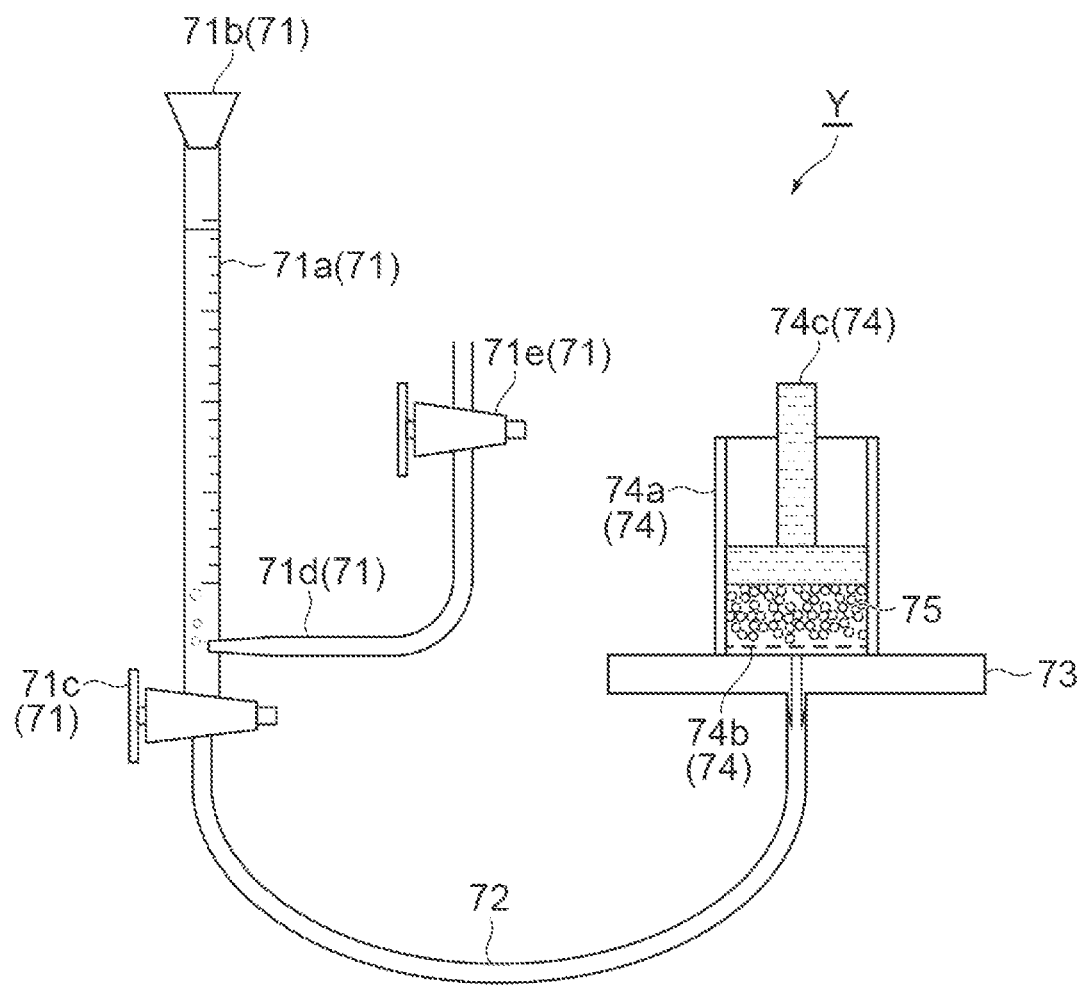
FIG. 4 is a schematic view showing a measuring device for a water absorption capacity of water-absorbing resin particles under a load.

A water absorption capacity (room temperature, 25° C.±2° C.) of the water-absorbing resin particles for a physiological saline solution under a load (under pressurization) was measured using a measuring device Y shown in FIG. 4. The measuring device Y is composed of a burette part 71, a conduit pipe 72, a measuring stand 73, and a measuring part 74 placed on the measuring stand 73. The burette part 71 includes a burette 71a extending in a vertical direction, a rubber stopper 71b disposed at an upper end of the burette 71a, a cock 71c disposed at a lower end of the burette 71a, an air introducing pipe 71d having one end extending to the burette 71a in the vicinity of the cock 71c, and a cock 71e disposed at the other end side of the air introducing pipe 71d. The conduit pipe 72 is attached between the burette part 71 and the measuring stand 73. An inner diameter of the conduit pipe 72 is 6 mm. A hole with a diameter of 2 mm is present in a center portion of the measuring stand 73, and the conduit pipe 72 is connected to the hole. The measuring part 74 includes a cylinder 74a (made of acrylic resin (plexiglass)), a nylon mesh 74b adhered to a bottom portion of the cylinder 74a, and a weight 74c. An inner diameter of the cylinder 74a is 20 mm. An aperture of the nylon mesh 74b is 75 μm (200 mesh). Then, at the time of measurement, water-absorbing resin particles 75 which are measurement targets are uniformly dispersed on the nylon mesh 74b. A diameter of the weight 74c is 19 mm, and a mass of the weight 74c is 120 g. The weight 74c can be placed on the water-absorbing resin particles 75 to apply a load of 4.14 kPa to the water-absorbing resin particles 75.

After 0.100 g of the water-absorbing resin particles 75 were put into the cylinder 74a of the measuring device Y, the weight 74c was placed thereon, and the measurement was started. The same volume of air as the physiological saline solution absorbed by the water-absorbing resin particles 75 was quickly and smoothly supplied to the inside of the burette 71a through the air introducing pipe, and therefore a reduced amount in water level of the physiological saline solution inside the burette 71a was an amount of the physiological saline solution absorbed by the water-absorbing resin particles 75. A scale of the burette 71a was engraved from 0 mL in increments of 0.5 mL, from the top to bottom direction. A scale Va of the burette 71a before the start of water absorption and a scale Vb of the burette 71a 60 minutes after the start of water absorption were read as water levels of the physiological saline solution, and a water absorption capacity under a load was calculated from the following formula. The results are shown in Table 1.

Water absorption capacity under load [mL/g]=$(Vb-Va)/0.1$

<Measurement of Value of (Non-pressurization Demand Wettability (DW) after 1 Minute>

Non-pressurization DW of the water-absorbing resin particles was measured using a measuring device shown in FIG. 1. The measurement was carried out five times for one type of water-absorbing resin particles, and an average value of three measurement values excluding a minimum value and a maximum value was obtained.

The measuring device has a burette part 1, a conduit pipe 5, a measuring stand 13, a nylon mesh sheet 15, a stand 11, and a clamp 3. The burette part 1 has a burette tube 21 on which a scale is engraved, a rubber stopper 23 for sealing an opening at an upper part of the burette tube 21, a cock 22 connected to a distal end of a lower part of the burette tube 21, an air introducing pipe 25 connected to the lower part of the burette tube 21, and a cock 24. The burette part 1 is fixed by the clamp 3. The flat plate-shaped measuring stand 13 has a through-hole 13a having a diameter of 2 mm and formed in the center portion of the measuring stand 13, and is supported by the height-variable stand 11. The through-hole 13a of the measuring stand 13, and the cock 22 of the burette part 1 are connected by the conduit pipe 5. An inner diameter of the conduit pipe 5 is 6 mm.

The measurement was performed in the environment of a temperature of 25° C. and a humidity of 60±10%. First, the cock 22 and the cock 24 of the burette part 1 were closed, and a 0.9% by mass saline solution 50 that had been adjusted to 25° C. was put into the burette tube 21 through the opening at the upper part of the burette tube 21. A concentration of 0.9% by mass of the saline solution is a concentration based on a mass of the saline solution. The opening of the burette tube 21 was sealed with the rubber stopper 23, and then the cock 22 and the cock 24 were opened. The inside of the conduit pipe 5 was filled with the 0.9% by mass saline solution 50 to prevent air bubbles from entering. A height of the measuring stand 13 was adjusted so that a height of a water surface of the 0.9% by mass saline solution, which had reached the inside of the through-hole 13a, was the same as a height of an upper surface of the measuring stand 13. After the adjustment, the height of the water surface of the 0.9% by mass saline solution 50 in the burette tube 21 was read by the scale on the burette tube 21, and this position was defined as a zero point (value read at 0 seconds).

The nylon mesh sheet 15 (100 mm×100 mm, 250 mesh, thickness about 50 μm) was laid in the vicinity of the through-hole 13 on the measuring stand 13, and a cylinder having an inner diameter of 30 mm and a height of 20 mm was placed on the center portion of the nylon mesh sheet. 1.00 g of water-absorbing resin particles 10a were uniformly dispersed in this cylinder. Thereafter, the cylinder was carefully removed to obtain a sample in which the water-absorbing resin particles 10a were dispersed in a circle shape in the center portion of the nylon mesh sheet 15. Then, the nylon mesh sheet 15 on which the water-absorbing resin particles 10a were placed was moved at a high speed to the extent that the water-absorbing resin particles 10a did not dissipate so that the center of the nylon mesh sheet was at the position of the through-hole 13a, and the measurement was started. A timing when air bubbles were first introduced from the air introducing pipe 25 into the burette tube 21 was defined as a start of water absorption (0 seconds).

An amount of decrease in the 0.9% by mass saline solution 50 in the burette tube 21 (that is, an amount of the 0.9% by mass saline solution absorbed by the water-absorbing resin particles 10a) was sequentially read by units of 0.1 mL, and a reduction in weight Wc (g) of the 0.9% by mass saline solution 50 was read 1 minute after the start of water absorption by the water-absorbing resin particles 10a. A value of non-pressurization DW after 1 minute was obtained from Wc by the following formula. The non-pressurization DW is a water absorption capacity per 1.00 g of the water-absorbing resin particles 10a.

Value of Non-Pressurization DW after 1 minute (mL/g)= Wc/1.00

<Preparation of Artificial Urine>

A solution was prepared by blending and dissolving components in ion exchange water so that inorganic salts were present as shown below. A small amount of Blue No. 1 was further blended therein, and thereby artificial urine (test solution) was prepared. The following concentrations are concentrations based on a total mass of the artificial urine.

Composition of Artificial Urine
  NaCl: 0.780% by mass
  $CaCl_2$: 0.022% by mass
  $MgSO_4$: 0.038% by mass
  Blue No. 1: 0.002% by mass <Artificial Urine Permeation Speed when Water-Absorbing Resin Particles Are-Swollen 10 Times>

(a) Installation of Measuring Device

Figure 2:
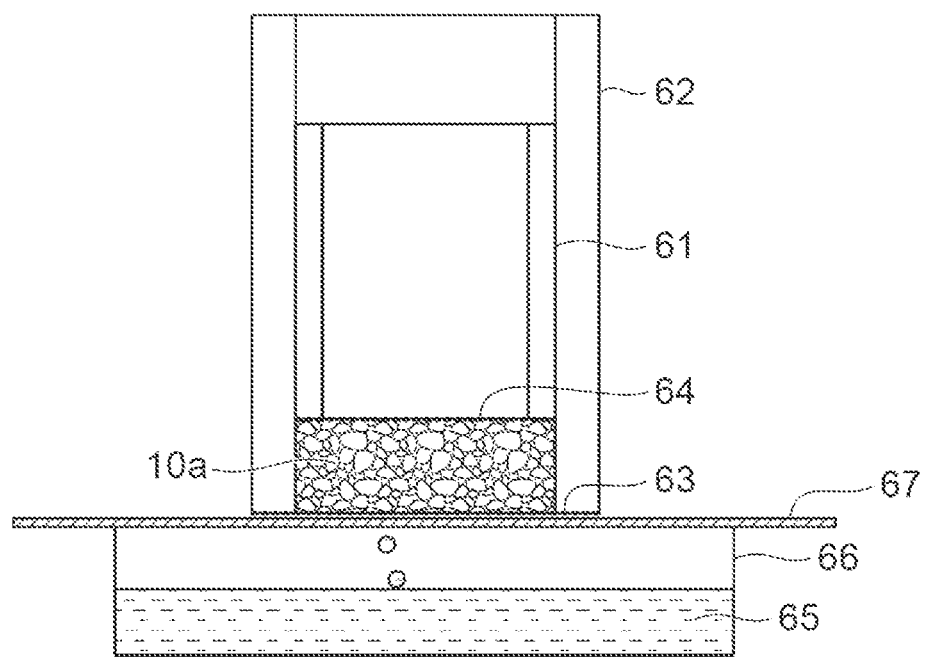
FIG. 2 is a schematic view showing a measuring device for an artificial urine permeation speed when water-absorbing resin particles are swollen 10 times.

As a measuring device, the one of which a schematic configuration is shown in FIG. 2 was used. A measuring part is composed of an acrylic resin cylindrical container (A) 61 which has an inner diameter of 19 mm, an outer diameter of 25 mm, a height of 120 mm, and a weight of about 30 g, and to which a nylon mesh sheet (250 mesh) 64 is adhered; an acrylic resin cylindrical container (B) 62 which has an inner diameter of 26 mm, an outer diameter of 40 mm, and a height of 140 mm, and to which a nylon mesh sheet 63 is adhered in the same manner; and swollen water-absorbing resin particles 10a. The cylindrical container (B) can move up and down inside the cylindrical container (A) without resistance. A petri dish 66 has an inner diameter of about 70 mm.

(b) Measurement of Liquid Permeation Speed

The measurement was performed in a room at about 25° C. and a humidity of 60±10%. 0.20 g of water-absorbing resin particles were uniformly put into the cylindrical container (B) 62, and the cylindrical container (A) 61 was inserted from above to form the measuring part. A mesh side of the measuring part was immersed in a petri dish having an inner diameter of 30 mm to which 1.8 g of artificial urine was put, and the water-absorbing resin particles were swollen for 10 minutes. Thereby, the water-absorbing resin particles were swollen 10 times.

A mass (Wd) was measured in a state where a dried wire mesh 67 having an aperture of 1.4 mm (100 mm×100 mm) was placed on the empty petri dish 66. Then, the measuring part containing the swollen water-absorbing resin particles 10a was placed on the center of the wire mesh 67. Then, 20 g of the artificial urine was added from an upper part of the cylindrical container (A) 61, and at the same time, a stopwatch was started. 30 seconds after the addition of the artificial urine, the measuring part containing the water-absorbing resin particles 10a was removed from the wire mesh 67. A total mass (We) of the petri dish 66, which contained the artificial urine 65 that had passed through the swollen water-absorbing resin particles 10a and flowed out, and the wire mesh 67 was measured until the lapse of 30 seconds (0.5 minutes) after the addition. An artificial urine permeation speed (g/min) was obtained by the following formula.

Artificial urine permeation speed (g/min)=(W−Wd)/0.5

<Permeation and Spreading Index>

A permeation and spreading index represented by the following formula was obtained.

Permeation and spreading index=value of non-pressurization DW after 1 minute+artificial urine permeation speed when water-absorbing resin particles are swollen 10 times <Performance of Water-Absorbing Resin Particles>

Table 1 shows the water-absorbing resin particles used in examples and comparative examples, and performances of the water-absorbing resin particles.

TABLE 1

| | Performance of water-absorbing resin particles | | | | |
|---|---|---|---|---|---|
| | Water absorption capacity for physiological saline solution [g/g] | Water absorption capacity under load [mL/g] | Value of non-pressurization DW after 1 minute [mL/g] | Artificial urine permeation speed when water-absorbing resin particles are swollen 10 times (g/min) | Permeation and spreading index |
| Example 1 | 57 | 20 | 16.2 | 1.6 | 17.8 |
| Example 2 | 51 | 25 | 7.8 | 12.3 | 20.1 |
| Example 3 | 59 | 22 | 9.2 | 3.3 | 12.5 |
| Example 4 | 59 | 22 | 18.8 | 3.0 | 21.8 |
| Comparative Example 1 | 60 | 18 | 0.7 | 0.0 | 0.7 |
| Comparative Example 2 | 68 | 17 | 3.4 | 0.0 | 3.4 |
| Comparative Example 3 | 54 | 28 | 3.2 | 5.2 | 8.4 |
| Comparative Example 4 | 44 | 26 | 2.0 | 31.0 | 33.0 |

<Inclination Leakage Test>

Leakage properties of the water-absorbing resin particles were evaluated by the following procedures i), ii), iii), iv) and v).

i) A strip-shaped adhesive tape (manufactured by DIATEX Co., Ltd., Piolan tape) having a length of 15 cm and a width of 5 cm was put on a laboratory table such that an adhesive surface faced up, and 3.0 g of the water-absorbing resin particles was evenly dispersed onto this adhesive surface. A stainless steel roller (mass 4.0 kg, diameter 10.5 cm, width 6.0 cm) was placed on the upper part of the dispersed water-absorbing resin particles, and this roller was caused to reciprocate three times between both ends of the adhesive tape in a longitudinal direction. Accordingly, a water-absorbing layer formed of the water-absorbing resin particles was formed on the adhesive surface of the adhesive tape.

ii) The adhesive tape was caused to stand vertically to remove excess water-absorbing resin particles from the water-absorbing layer. The roller was placed on the water-absorbing layer again and caused to reciprocate three times between both ends of the adhesive tape in the longitudinal direction.

iii) In a room at a temperature of 25±2° C., an acrylic resin plate having a rectangular flat main surface with a length of 30 cm and a width of 55 cm was fixed such that its width direction was parallel to the horizontal plane, and an angle between its main surface and the horizontal plane was 30 degrees. The adhesive tape on which the water-absorbing layer was formed was bonded to the main surface of the fixed acrylic plate such that the water-absorbing layer was exposed and in a direction in which the longitudinal direction of the adhesive tape was perpendicular to the width direction of the acrylic resin plate.

iv) Using a micropipette (PIPETMAN Neo P1000N manufactured by M&S Instruments Inc), 0.25 mL of a test solution at a liquid temperature of 25° C. was entirely injected within 1 second into a position about 1 cm from the upper end of the water-absorbing layer, from a height of about 1 cm from the surface.

v) 30 seconds after the start of the injection of the test solution, a maximum value of a moving distance of the test solution injected into the water-absorbing layer was read and recorded as a diffusion distance D. The diffusion distance D is a distance on the main surface connecting a dropping point (injection point) and the longest reaching point with a straight line in a direction perpendicular to the horizontal plane of the short side of the acrylic resin plate. When the diffusion distance D was 14 cm or longer, liquid leakage occurred.

TABLE 2

| Example·Comparative Example | Inclination leakage test Diffiasion distance [cm] |
|---|---|
| Example 1 | 9.0 |
| Example 2 | 10.0 |
| Example 3 | 12.0 |
| Example 4 | 7.5 |
| Comparative Example 1 | 14 or more Leakage occurred |
| Comparative Example 2 | 14 or more Leakage occurred |
| Comparative Example 3 | 14 or more Leakage occurred |
| Comparative Example 4 | 14 or more Leakage occurred |

Based on the results in Table 2, it was shown that the water-absorbing resin particles obtained in the examples can inhibit liquid leakage as compared with the water-absorbing resin particles obtained in the comparative examples.

<Production of Absorbent and Absorbent Article>

[Production of Absorbent Article Containing Water-Absorbing Resin Particles of Example 1]

10 g of the water-absorbing resin particles of Example 1 and 9.5 g of pulverized pulp were uniformly mixed by air papermaking using an air flow type mixer (Padfonner manufactured by OTEC Co., Ltd.), and thereby a sheet-shaped absorbent having a size of 12 cm×32 cm was produced. The absorbent was disposed on a tissue paper (core wrap) having a basis weight of 16 g/m². A tissue paper (core wrap), and an air through non-woven fabric (liquid-permeable sheet), which is a short-fiber non-woven fabric, were laminated on the absorbent in this order. A load of 588 kPa was applied to this laminate for 30 seconds. Furthermore, a polyethylene liquid-impermeable sheet having a size of 12 cm×32 cm was bonded to a surface on the side opposite to the air through non-woven fabric, and thereby an absorbent article for testing (absorbent article containing the water-absorbing resin particles of Example 1) was produced. A fabric weight per unit area of the air through non-woven fabric used was 17 g/m².

In the absorbent article, a basis weight of the water-absorbing resin particles was 280 g/m², and a basis weight of the pulverized pulp (hydrophilic fibers) was 260 g/m².

[Production of Absorbent Articles Containing Water-Absorbing Resin Particles of Examples 2 to 4]

Absorbent articles respectively containing the water-absorbing resin particles of Examples 2 to 4 were produced in the same manner as in the absorbent article containing the water-absorbing resin particles of Example 1 except that the water-absorbing resin particles were changed to the water-absorbing resin particles of Examples 2 to 4.

[Production of Absorbent Articles Containing Water-Absorbing Resin Particles of Comparative Examples 1 to 4]

Absorbent articles respectively containing the water-absorbing resin particles of Comparative Examples 1 to 4 were produced in the same manner as in the absorbent article containing the water-absorbing resin particles of Example 1 except that the water-absorbing resin particles were changed to the water-absorbing resin particles of Examples 5 to 8.

<Slope Absorption Test of Absorbent Article>

Figure 5:
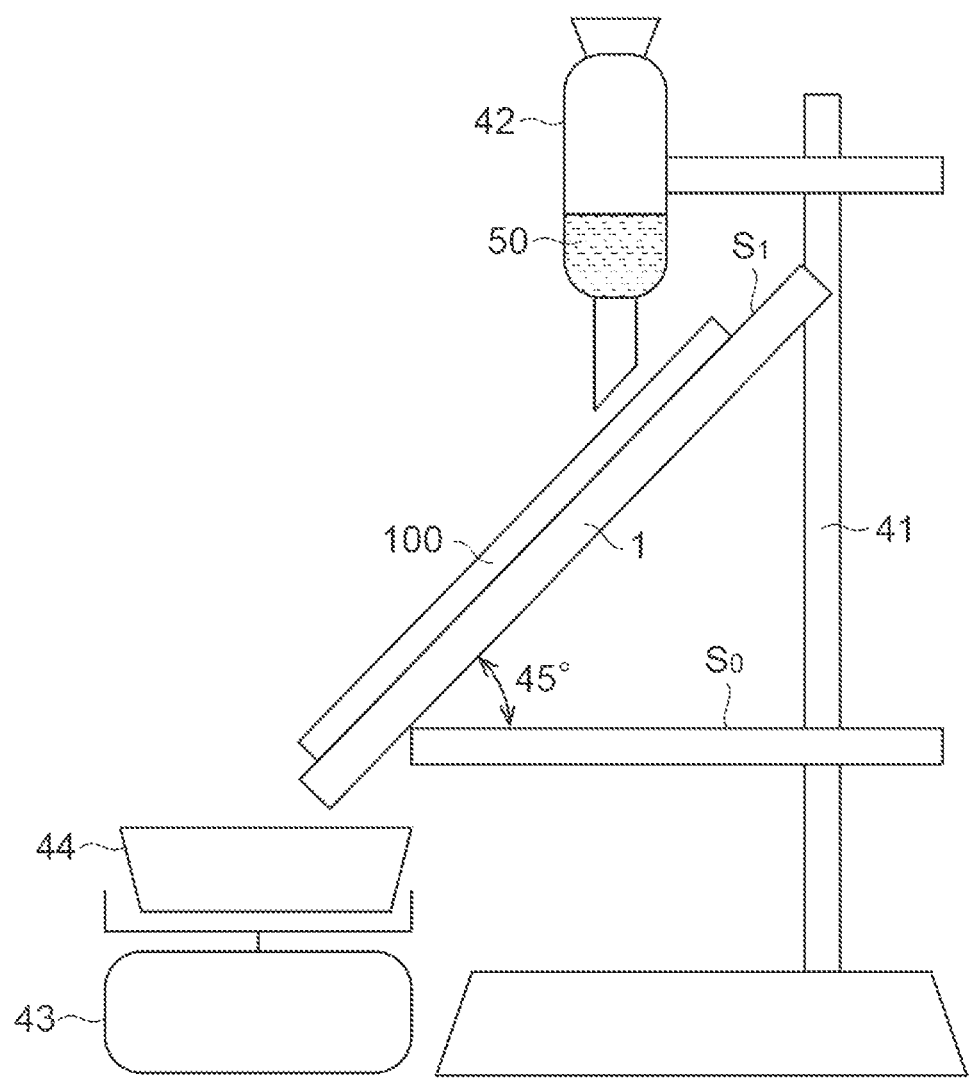
FIG. 5 is a schematic view showing a method for evaluating liquid leakage properties of an absorbent article.

FIG. 5 is a schematic view showing a method for evaluating leakage properties of an absorbent article. A support plate 1 (herein referred to as an acrylic resin plate, and hereinafter also referred to as an inclined plane $S_1$) with a length of 45 cm and having a flat main surface was fixed by a stand 41 in a state of being inclined at 45±2 degrees with respect to a horizontal plane $S_0$. An absorbent article 100 for testing was bonded onto the inclined plane $S_1$ of the fixed support plate 1 in a room at a temperature of 25±2° C. such that a longitudinal direction of the absorbent article 100 was along a longitudinal direction of the support plate 1. Next, a test solution 50 (artificial urine) adjusted to 25±1° C. was added dropwise from a dropping funnel 42 vertically disposed above the absorbent article toward a position 8 cm, in an upper direction, from the center of an absorbent in the absorbent article 100. 80 mL of the test solution was added dropwise at a time at a speed of 8 mL/sec. A distance between a tip end of the dropping funnel 42 and the absorbent article was 10±1 mm. The test solution was repeatedly added under the same conditions at intervals of 10 minutes from the start of the first addition of the test solution. The test solution was added until leakage was observed.

In a case where the test solution that was not absorbed by the absorbent article 100 leaked out from a lower part of the support plate 1, the leaked test solution was recovered in a metal tray 44 disposed below the support plate 1. A weight (g) of the recovered test solution was measured by a balance 43, and this value was recorded as an amount of leakage. The amount of leakage was subtracted from a total amount of the test solution added to calculate an amount of absorption until the leakage occurred. It is judged that as this numerical value becomes large, liquid leakage is unlikely to occur when the absorbent article is worn.

TABLE 3

| | Absorbent article ||||||||
|---|---|---|---|---|---|---|---|---|
| | Amount of leakage [g] |||||| Number of addition until leakage occurs | Amount of absorption until leakage occurs |
| | 1st | 2nd | 3rd | 4th | 5th | 6th | | |
| Example 1 | 0 | 0 | 0 | 0 | 7 | | 5 | 393 |
| Example 2 | 0 | 0 | 0 | 0 | 3 | | 5 | 397 |
| Example 3 | 0 | 0 | 0 | 0 | 26 | | 5 | 374 |
| Example 4 | 0 | 0 | 0 | 0 | 0 | 10 | 6 | 470 |
| Comparative Example 1 | 0 | 0 | 0 | 6 | 43 | | 4 | 314 |
| Comparative Example 2 | 0 | 0 | 0 | 8 | 35 | | 4 | 312 |
| Comparative Example 3 | 0 | 0 | 0 | 5 | 19 | | 4 | 315 |
| Comparative Example 4 | 0 | 0 | 0 | 21 | 12 | | 4 | 299 |

Based on the results in Table 3, it was shown that the water-absorbing resin particles obtained in the examples can inhibit liquid leakage as compared with the water-absorbing resin particles obtained in the comparative examples.

REFERENCE SIGNS LIST

1: burette part
3: clamp
5: conduit pipe
10: absorbent
10a: water-absorbing resin particle
10b: fiber layer
11: stand
13: measuring stand
13a: through-hole
15: nylon mesh sheet
20a, 20b: core wrap
21: burette tube
22: cock
23: rubber stopper
24: cock
25: air introducing pipe
30: liquid-permeable sheet
40: liquid-impermeable sheet
50: 0.9% by mass saline solution
61: cylindrical container (A)
62: cylindrical container (B)
63, 64: nylon mesh sheet
65: artificial urine
66: petri dish
67: wire mesh
71: burette part
71a: burette
71b: rubber stopper
71c: cock
71d: air introducing pipe
71e: cock
72: conduit pipe
73: measuring stand
74: measuring part
74a: cylinder
74b: nylon mesh
74c: weight
100: absorbent article
$S_0$: horizontal plane
$S_1$: inclined plane

The invention claimed is:

1. Water-absorbing resin particles comprising:
   a polymer particle comprising a crosslinked polymer having a monomer unit derived from an ethylenically unsaturated monomer including at least one compound selected from the group consisting of (meth)acrylic acid and a salt thereof; and
   a plurality of inorganic particles disposed on a surface of the polymer particle,
   wherein a proportion of a (meth)acrylic acid and a salt thereof is 70 to 100 mol % with respect to a total amount of monomer units in the crosslinked polymer,
   a permeation and spreading index represented by Formula (1) is 10.0 or higher, and
   a water absorption capacity for a physiological saline solution is 50.0 g/g or more, Formula (1):

permeation and spreading index=value of non-pressurization demand wettability (DW) after 1 minute (mL/g)+artificial urine permeation speed when water-absorbing resin particles are swollen 10 times (g/min)        (1).

2. The water-absorbing resin particles according to claim 1,
   wherein the permeation and spreading index is 13.0 or higher.

3. The water-absorbing resin particles according to claim 1,
   wherein the value of non-pressurization DW after 1 minute is 3.0 mL/g or more.

4. The water-absorbing resin particles according to claim 1,
   wherein the permeation and spreading index is 14.0 or higher.

5. The water-absorbing resin particles according to claim 1,
   wherein the permeation and spreading index is 14.0 or higher and 25.0 or lower.

6. The water-absorbing resin particles according to claim 1,
   wherein the value of non-pressurization DW after 1 minute is 7.0 mL/g or more.

7. The water-absorbing resin particles according to claim 1, wherein the artificial urine permeation speed when the water-absorbing resin particles are swollen 10 times is 1.0 g/min or more.

8. The water-absorbing resin particles according to claim 1,
   the artificial urine permeation speed when water-absorbing resin particles are swollen 10 times is 1.0 g/min or more and 15.0 g/min or less.

9. The water-absorbing resin particles according to claim 1,
   wherein a water absorption capacity of the water-absorbing resin particles for a physiological saline solution under a load is 10 to 40 mL/g.

10. The water-absorbing resin particles according to claim 1,
    wherein a water absorption capacity of the water-absorbing resin particles for a physiological saline solution under a load is 22 to 28 mL/g.

11. The water-absorbing resin particles according to claim 1,
    wherein a median particle size of the water-absorbing resin particles is 250 to 850 μm.

12. The water-absorbing resin particles according to claim 1,
wherein a median particle size of the water-absorbing resin particles is 300 to 600 μm.

13. The water-absorbing resin particles according to claim 1,
wherein a water absorption capacity for a physiological saline solution is 50.0 g/g or more and 70 g/g or less.

14. An absorbent article comprising:
a liquid-impermeable sheet;
an absorbent; and
a liquid-permeable sheet,
wherein the liquid-impermeable sheet, the absorbent, and the liquid-permeable sheet are disposed in this order, and
the absorbent comprises the water-absorbing resin particles according to claim 1.

15. A method for manufacturing an absorbent article, the method comprising:
sorting out water-absorbing resin particles in which a permeation and spreading index represented by Formula (1) is 10.0 or higher, and a water absorption capacity for a physiological saline solution is 50.0 g/g or more; and
disposing an absorbent containing the sorted water-absorbing resin particles between a liquid-impermeable sheet and a liquid-permeable sheet,
wherein the water-absorbing resin particles comprise
a polymer particle containing a crosslinked polymer having a monomer unit derived from an ethylenically unsaturated monomer including at least one compound selected from the group consisting of (meth) acrylic acid and a salt thereof, and
a plurality of inorganic particles disposed on a surface of the polymer particle, and
a proportion of a (meth)acrylic acid and a salt thereof is 70 to 100 mol % with respect to a total amount of monomer units in the crosslinked polymer, Formula (1):

$$\text{permeation and spreading index} = \text{value of non-pressurization } DW \text{ after 1 minute (mL/g)} + \text{artificial urine permeation speed when water-absorbing resin particles are swollen 10 times (g/min)} \qquad (1).$$

16. The method according to claim 15,
wherein the value of non-pressurization $DW$ after 1 minute of the sorted water-absorbing resin particles is 3.0 mL/g or more.

* * * * *